United States Patent [19]

Ninagawa et al.

[11] Patent Number: 4,511,751
[45] Date of Patent: Apr. 16, 1985

[54] PROCESS FOR PRODUCING ISOPRENE

[75] Inventors: Yoichi Ninagawa; Osamu Yamada; Tsumoru Renge, all of Hasaki; Sunao Kyo, Abiko; Takayoshi Osaki, Kurashiki; Koichi Kushida, Ibaraki, all of Japan

[73] Assignee: Kuraray Company, Ltd., Kurashiki, Japan

[21] Appl. No.: 540,870

[22] Filed: Oct. 11, 1983

[30] Foreign Application Priority Data

| Oct. 14, 1982 | [JP] | Japan | 57-180759 |
| Dec. 9, 1982 | [JP] | Japan | 57-216500 |
| Dec. 13, 1982 | [JP] | Japan | 57-219096 |
| Dec. 24, 1982 | [JP] | Japan | 57-229192 |
| Apr. 4, 1983 | [JP] | Japan | 58-59654 |
| Apr. 13, 1983 | [JP] | Japan | 58-66147 |
| May 20, 1983 | [JP] | Japan | 58-89827 |
| Jun. 20, 1983 | [JP] | Japan | 58-111485 |

[51] Int. Cl.³ .............................................. C07C 11/18
[52] U.S. Cl. ................................... 585/608; 585/609; 585/611
[58] Field of Search ......................... 585/608, 609, 611

[56] References Cited

U.S. PATENT DOCUMENTS

| 2,350,485 | 6/1944 | Arundale et al. | 585/608 |
| 3,890,404 | 6/1975 | Takagi et al. | 585/608 |
| 4,067,923 | 1/1978 | Belyreu et al. | 585/608 |

Primary Examiner—Curtis R. Davis
Attorney, Agent, or Firm—Oblon, Fisher, Spivak, McClelland & Maier

[57] ABSTRACT

A process for producing isoprene in good yield is provided. The process is characterized in that isobutene and/or tertiary butanol and a formaldehyde source are fed, together with water, into an acidic aqueous solution continuously or intermittently while maintaining the reaction pressure in an adequate range and at the same time distilling off the product isoprene and unreacted starting materials, together with water, from the reaction zone.

13 Claims, 1 Drawing Figure

FIG. 1

PROCESS FOR PRODUCING ISOPRENE

BACKGROUND OF THE INVENTION

1. Field of the Invention

This invention relates to a process for producing isoprene by reacting isobutene and/or tertiary butanol with formaldehyde.

2. Description of the Prior Art

Attempts to synthesize isoprene in one step by reacting isobutene or a precursor thereof with formaldehyde have been made repeatedly and a number of processes have been proposed.

For instance, Japanese Kokai Tokkyo Koho (laid-open patent application) No. 46-6,963 discloses a gaseous phase process using a phosphoric acid-calcium oxide-chromium oxide catalyst. However, this process is far from practicable because the catalyst life is short.

Liquid phase processes using various aqueous acid solutions as the catalysts are disclosed in U.S. Pat. No. 3,890,404, Japanese Patent Publication No. 52-30,483 and Japanese Kokai Tokkyo Koho No. 57-130,928. In U.S. Pat. No. 3,890,404, for instance, it is indicated that when the reaction was conducted at 160° C. for 18 minutes using $FeCl_2$ as the catalyst, isoprene was formed in a yield of 82% of the formaldehyde basis (Example 32). However, in check experiments performed by the present inventors, the procedures described in Example 32 of U.S. Pat. No. 3,890,404, Example 2 of Japanese Patent Publication No. 52-30,483 and Example 8 of Japanese Kokai Tokkyo Koho No. 57-130,928 gave isoprene yields of about 50% or below, as shown later in Reference Examples. Other examples than the above, when checked, gave nothing but similarly low isoprene yields.

U.S. Pat. No. 4,067,923 discloses that isoprene was formed in an yield exceeding 70% when the reaction was carried out batchwise or in the manner of a piston flow using a sulfanilic acid as the catalyst. However, check experiments by the present inventors revealed that the main product was 4,4-dimethyl-1,3-dioxane and that isoprene was formed in a very small amount (refer to Reference Example 5 to be mentioned later). According to the above cited reference, the reaction is carried out in a closed system at a temperature not lower than the critical point of isobutene. However, such reaction conditions require a high pressure, hence a large cost of equipment.

Furthermore, U.S. Pat. No. 2,350,485 describes various reaction modes for producing conjugated dienes by the reaction of an olefin and an aldehyde. However, the disclosure contains only one example which is concerned with the reaction of 2-methyl-2-butene with formaldehyde in a closed system, and, according to said example, the yield of 2,3-dimethyl-1,3-butadiene is as low as 23%. When the present inventors reacted isobutene with formaldehyde under the same conditions as in said example, the yield of isobutene was similar to that of 2,3-dimethyl-1,3-butadiene just mentioned above.

As mentioned hereinabove, the one-step production of isoprene from isobutene and/or tertiary butanol and formaldehyde involves various problems to be solved. This is one of the major reasons why the so-called two-step process which involves the production of 4,4-dimethyl-1,3-dioxane as an intermediate has been employed for the commercial production of isoprene.

SUMMARY OF THE INVENTION

Intensive research by the present inventors in order to solve these prior art technological problems encountered in the one-step liquid-phase process for produing isoprene has now led to the present invention. According to the invention, isoprene can be produced in good yield by reacting isobutene and/or tertiary butanol with formaldehyde in an acidic aqueous solution under the following conditions:

(a) that the acidic aqueous solution is present in the reaction zone, (b) that isobutene and/or tertiary butanol, a formaldehyde source and water are fed to said reaction zone continuously or intermittently, and (c) that isoprene, water, unreacted starting materials and other low-boiling components are distilled off from said reaction zone, the amounts of said isobutene and/or tertiary butanol and formaldehyde source being fed to said reaction zone being such that the isobutene/tertiary butanol (i.e., isobutene and/or tertiary butanol) -to-formaldehyde molar ratio in the charge is at least 3 and the pressure in the reaction system being maintained at a level 1.1 to 2.5 times the vapor pressure at the reaction temperature of the acidic aqueous solution existing in the reaction zone, said isobutene/tertiary butanol-to-formaldehyde molar ratio being calculated by calculating the amount of the formaldehyde source in formaldehyde equivalent when said source is other than formaldehyde. The vapor pressure at the reaction temperature of the acidic aqueous solution is a physical constant definitely determined depending on the kind and concentration of the acidic substance containing in said acidic aqueous solution.

In accordance with another aspect of the present invention, isoprene can be produced in more improved yield by conducting the reaction in the manner characterized in:

(a) that the acidic aqueous solution is present in plural reaction zones connected in series, (b) that isobutene and/or tertiary butanol is fed to the first reaction zone continuously or intermittently while a formaldehyde source and water are fed to each reaction zone continuously or intermittently, (c) that isoprene, water, unreacted starting materials and other low-boiling components are distilled off from each reaction zone except the last one and fed to the subsequent reaction zone, and (d) that isoprene, water, unreacted starting materials and other low-boiling components are distilled off from the last reaction zone, the amounts of said isobutene and/or tertiary butanol and formaldehyde source being fed to each reaction zone being such that the isobutene/tertiary butanol (i.e., isobutene and/or tertiary butanol) -to-formaldehyde molar ratio in the charge is at least 3 and the pressure in the reaction system being maintained at a level 1.1 to 2.5 times the vapor pressure at the reaction temperature of the acidic aqueous solution existing in the reaction zone, said isobutene/tertiary butanol-to-formaldehyde molar ratio being calculated by calculating the amount of the formaldehyde source in formaldehyde equivalent when said source is other than formaldehyde.

The process according to the invention have many advantages. For instance, the process is good in workability and stability during working, the catalyst life is long, the reaction can be conducted at a relatively low temperature and under a relatively low pressure, and therefore the cost of equipment can be reduced.

When the desired product is more volatile than the reactants, the yield of the product can generally be increased very effectively by conducting the reaction while distilling off said product. In this case, the concentration of the reactants in the liquid existing in the reaction zone becomes higher and the concentration of the product lower as compared with the distillate, so that side reactions are inhibited and as a result the yield increases. A typical example can be seen in the production of isoprene by dehydration of 3-methyl-1,3-butanediol (refer to Japanese Kokai Tokkyo Koho No. 54-163,504).

On the other hand, when using reactants more volatile than the product, the reaction is performed while distilling off the product, an improved yield can hardly be expected but the yield generally tends to decrease because the concentration of the reactants in the liquid existing in the reaction zone becomes lower and the concentration of the product higher as compared with the distillate. For the reaction of isobutene and formaldehyde, the mode of reaction with simultaneous distillation seems disadvantageous, since isobutene is much more volatile than the product, namely isoprene. This is presumably the reason why, among many reports so far made concerning the reaction of isobutene and formaldehyde, none mentioned an embodiment of such reaction-with-distillation process. The above-cited U.S. Pat. No. 2,350,485 refers to, as one of the modes of reaction, the mode of conducting the reaction while distilling off the products and reactants but does not mention any specific reaction conditions at all. There is not found any mention of the influence on the yield as exerted by this mode of reaction to be conducted while distilling off the product and reactants. The present inventors conducted the reaction of isobutene and/or tertiary butanol with formaldehyde in an acidic aqueous solution with simultaneous distillation and found that isoprene can be formed in high yields, which could not be attained by the reaction in a closed system, by maintaining, as mentioned above, the pressure within the reaction system and the isobutene/tertiary butanol-to-formaldehyde molar ratio each within an adequate range.

DETAILED DESCRIPTION OF THE INVENTION

In the following description, isobutene and/or tertiary butanol is sometimes referred to as "$C_4$" and the formaldehyde source as "FA". Furthermore, the number of moles of $C_4$ sometimes referred to as "C", the number of moles of formaldehyde as "F", and the vapor pressure at the reaction temperature of the acidic aqueous solution as "Pw".

The process according to the invention consists in that $C_4$, FA and water are fed into an acidic aqueous solution continuously or intermittently while distilling off isoprene together with water, unreacted starting materials and other low-boiling components from the reaction system and that, while carrying out the reaction in the above manner, the ratio C/F (molar ratio between $C_4$ and FA to be fed to the reaction zone) and the pressure of the reaction system are maintained within an adequate range respectively. Said "other low-boiling components" include substances which are distilled off from the reaction zone together with water under the reaction conditions, for instance volatile by-products.

In carrying out the reaction according to the process of the invention, the ratio C/F (molar ratio between $C_4$ and FA to be fed to the reaction zone) is required to be at least 3. When said ratio C/F is smaller than 3, the yield of isoprene will drop. From the viewpoint of selectivity, a greater C/F ratio is more preferred, hence, in a strict sense, there is no upper limit thereto. However, excessively large C/F ratios do not always result in efficiently improved isoprene yields. When a single reaction zone is used, the heat consumption increases as the ratio C/F increases. Therefore, in such case, it is generally recommended that C/F should be not more than 20. When the reaction is conducted in plural reaction zones, the heat consumption depends on the ratio C/F between $C_4$ and FA to be fed throughout all the reaction zones. Therefore, the ratio C/F between $C_4$ and FA to be fed throughout all the reaction zones should preferably be not more than 20. In that case, the ratio C/F for each reaction zone is selected within an adequate range such that the overall ratio C/F for all the reaction zones does not exceed 20.

Conditions more favorable to the formation of isoprene can be obtained by using plural reaction zones and thereby increasing the ratio C/F between the reactants to be fed to each reaction zone without varying the total volume of the reaction zones and the ratio C/F between the reactants to be fed throughout all the reaction zones. Moreover, since not only the rate of feeding FA but also the rate of feeding water, the pressure within the reaction system, the reaction temperature, the acidity of the acidic aqueous solution and the volume of the reaction zone can be selected in an adequate manner for each reaction zone, the increase in isoprene yield as caused by increasing the ratio C/F between the reactants to be fed to each reaction zone can exceed the loss of isoprene due to consecutive reactions thereof and, as a result, an increased isoprene yield can be achieved at the same overall C/F ratio as compared with the case in which the reaction is conducted in a single reaction zone. In other words, the ratio C/F between the reactants to be fed throughout all the reaction zones as required for achieving the same isoprene yield can be reduced as compared with the case in which the reaction is performed in a single reaction zone, so that the amount of $C_4$ to be used and the amount of water to be evaporated can be reduced, whereby isoprene can be produced advantageously from the energy viewpoint. For increasing the isoprene yield using plural reaction zones while maintaining the ratio C/F between the reactants to be fed throughout all the reaction zones at a constant value, the number of reaction zones should preferably be greater. However, the yield-increasing effect is maximal when the number of reaction zones is increased from 1 to 2. Said effect decreases as said number is increased from 2 to 3, from 3 to 4, and so on. Generally, the number of reaction zones is selected within the range of 2-4 in view of the ratio C/F between the reactants to be fed to each reaction zone as well as the complexity of reaction operations. While it is preferable to feed the whole amount of $C_4$ to be subjected to reaction to the first reaction zone, it is also possible to feed part thereof to the second and subsequent reaction zones. Generally, however, this offers no particular advantage. FA, another starting material, is fed dividedly to the reaction zones. The proportions of FA for the respective reaction zones can adequately be decided in view of the amount and acidity of the acidic aqueous solution in each reaction zone.

From the energy viewpoint, the vapor from a reaction zone as it is in the gaseous form is preferably fed to the next reaction zone, although it may be condensed wholly or partly prior to submission to the next reaction zone. For smooth passage of the distillate, a later reaction zone is preferably placed under a lower reaction system pressure. Therefore, for achieving favorable reaction results and smooth progress of the reaction, the amount of water to be fed to each reaction zone is selected in an adequate manner so that a later reaction zone is under a lower reaction system pressure while the pressure of the reaction system maintaining the above relation. The reaction temperature and the acidity of the acidic aqueous solution may be varied according to the respective reaction zones or maintained at constant levels throughout all the reaction zones.

Since, as mentioned above, $C_4$ is used in excess of formaldehyde in carrying out the process according to the invention, most of $C_4$ fed into the acidic aqueous solution distills off in the unreacted form. This can be separated from other components and reused. The unreacted $C_4$ has a composition close to the equilibrium mixture of isobutene and tertiary butanol under the reaction conditions. Therefore, even when either one of isobutene and tertiary butanol is subjected to the reaction, the recycling feed, if the unreacted $C_4$ is recycled to the reaction, necessarily becomes a mixture of isobutene and tertiary butanol.

When the reaction mode comprising feeding $C_4$, FA and water, optionally together with a low-boiling component which is inert under the reaction conditions, into an acidic aqueous solution while distilling off isoprene and water, together with other low-boiling components, from the reaction zone is employed, the proportion between each component evaporable from the reaction zone and water can be controlled by adjusting the pressure of the reaction system. Thus, when the pressure of the reaction system becomes high, the proportion of water to the sum of other components in the distillate becomes decreased, whereas, when the reaction system pressure is low, a converse phenomenon takes place. For merely causing the reaction to proceed, any pressure higher than Pw can be selected as the pressure of the reaction system. However, it has been found that, for producing isoprene in good selectivity and in an economically advantageous manner, the pressure within the reaction system (when a low-boiling compound inert under the reaction conditions is fed, the pressure after subtraction of the partial pressure thereof) is required to be within the range of 1.1 to 2.5 times Pw. When said pressure exceeds 2.5×Pw, the isoprene yield becomes markedly decreased. This tendency is apparently seen in selectivity to isoprene based on $C_4$. If the pressure within the reaction system is lower than 1.1×Pw, then the conversion of formaldehyde decreases and, in addition, the proportion of water to isoprene in the distillate increases, leading to an increased consumption of heat energy, although the decrease in isoprene yield is not significant.

The formaldehyde source to be used in practicing the invention is, for instance, an aqueous formaldehyde solution or gaseous formaldehyde. Trioxane, paraformaldehyde and others which decompose under the reaction conditions to give formaldehyde may also be used. Formals such as methylal are also usable. Since water is fed to the reaction zone and formaldehyde takes the form of aqueous solution in the reaction zone, it is advantageous from the operation viewpoint to use an aqueous formaldehyde solution as the formaldehyde source.

The isobutene and tertiary butanol to be used in the process according to the present invention may contain other hydrocarbons as well as 3-methyl-1,3-butanediol, 3-methyl-2-buten-1-ol, 3-methyl-3-buten-1-ol, 3-methyl-1-buten-3-ol, methyl isopropyl ketone, 2-methylbutanal, methyl tert-butyl formal, 4,4-dimethyl-1,3-dioxane, 4-methyl-5,6-dihydro-2H-pyran, and the like. Alkyl tert-butyl ethers, such as methyl tert-butyl ether, which give isobutene and/or tertiary butanol under reaction conditions may also be used.

The amount of water to be fed to the reaction zone is generally adjusted so that the amount of the acidic aqueous solution in the reaction zone can be maintained at a constant level. The amount is decided based on the amount of water distilled off from the reaction zone and the increment or decrement in water amount as caused by the reaction. The ratio of the number of moles of water distilled off from the reaction zone to the number of moles of the starting materials and product depends on the pressure in the reaction system. Since the number of moles of the starting materials and product distilled off is almost equal to the number of moles of $C_4$, the proportion of water distilled off and $C_4$ fed is decided by the pressure in the reaction system. Therefore, the amount of water can be decided taking into consideration of the reaction system pressure, the $C_4$-feeding rate, and the increment or decrement in water amount as caused by the reaction.

In the practice of the invention, it is possible to perform the reaction while feeding, as desired, a low-boiling compound inert under the reaction conditions, together with the reactants, into the acidic aqueous solution. The low-boiling inert compound mentioned above includes those compounds which do not undergo substantial change in nature during the reaction, such as hydrocarbons containing 1 to 10 carbon atoms, typical representatives of which are n-propane, n-butane, n-hexane and cyclohexane, and inert gases such as nitrogen.

The preferred rate of feeding FA to the reaction zone is decided taking into consideration the acidity of the acidic aqueous solution in the reaction zone, the reaction temperature and the pressure in the reaction system. For increasing said FA feeding rate, it is necessary to increase the acidity of the acidic aqueous solution or raise the reaction temperature, and in that case there arises the problem of corrosion of the reaction vessel. Generally, therefore, the FA-feeding rate is preferably selected at a level not exceeding 3 moles (as formaldehyde) per kilogram of the acidic aqueous solution per hour. Although there is no lower limit in a strict sense on the FA-feeding rate, the formaldehyde source-feeding rate should preferably be not less than 0.2 mole (as formaldehyde) per kilogram of the acidic aqueous solution per hour because excessively small feeding rates require enlarged reaction vessel sizes, which are disadvantageous from the equipment viewpoint.

The reaction temperature which is preferred in practicing the present invention is generally selected within the range of 150°–220° C. taking into consideration the acidity of the acidic aqueous solution in the reaction zone. Reaction temperatures below 150° C. result in decreased selectivity to isoprene even when the acidity of the acidic aqueous solution is increased so as to maintain the reaction rate at a constant level. Reaction temperatures exceeding 220° C. result in decreased conversion of formaldehyde under the conditions which give a maximal selectivity to isoprene, although the decrease in isoprene selectivity is not remarkable. When the reaction conditions are selected in a manner such that a high formaldehyde conversion can be attained, the isoprene yield decreases as a result of secondary reactions of isoprene.

The catalyst to be used in the process according to the present invention includes acidic substances such as inorganic acids, organic acids, and salts thereof. These are used in the reaction zone in the form of an aqueous solution. The preferable concentration of said aqueous solution depends on the kind of the acidic substance, the reaction temperature and the FA-feeding rate, among others but generally is selected such that the acidic aqueous solution has a pH of 0.5 to 2.5. When the pH of the acidic aqueous solution exceeds 2.5, a remarkable decrease in isoprene yield will result, whereas when said pH is below 0.5, remarkable corrosion of the reaction apparatus may result in addition to a remarkable decrease in isoprene yield. Preferred species of said acidic substance are low-volatile or nonvolatile ones and include inorganic acids, such as phosphoric acid, sulfuric acid and boric acid, heteropolyacids, such as tungstosilicic acid and tungstophosphoric acid, organic acids, such as p-toluenesulfonic acid, benzenesulfonic acid, trifluoromethanesulfonic acid and oxalic acid, and acidic salts, such as sodium hydrogen sulfate. These acidic substances may be used in combination of two or more of them. The combination of boric acid and phosphoric acid is especially recommendable. Preferably, an aqueous mixed acid solution containing 15–30 percent by weight of boric acid and 0.5–5 percent by weight of phosphoric acid is used, whereby a high isoprene yield can be obtained and at the same time the corrosiveness can be much reduced as compared with the use of phosphoric acid having the same concentration. When the boric acid concentration in the above mixed aqueous solution is below 15 percent by weight, the corrosiveness may increase. When the boric acid concentration exceeds 30 percent by weight, the isoprene yield will decrease. On the other hand, when the phosphoric acid concentration is below 0.5 percent by weight, an increased reaction temperature is required for achieveing a practical reaction rate and as a result the corrosiveness-reducing effect becomes small. When the phosphoric acid concentration exceeds 5.0 percent by weight, a satisfactory corrosiveness-reducing effect cannot be obtained although the corrosion is inhibited to a certain extent as compared with the case in which phosphoric acid is used alone.

The results of stainless steel corrosion test in an aqueous phosphoric acid solution and in a mixed aqueous solution of phosphoric acid and boric acid are shown below in Table 1. The tests were conducted in the following manner.

A 1,000-ml pressure vessel made of glass equipped with thermometer, pressure gauge and magnetic stirrer was charged with 600 g of an aqueous acid solution having the composition indicated in Table 1. Formaldehyde was added to the aqueous acid solution to a concentration of 3,000 ppm so as to simulate the reaction conditions in the actual reaction system. An SUS316 stainless steel testpiece (5 cm × 1 cm × 0.3 cm) was polished with No. 240 sandpaper and then with No. 1,000 sandpaper, washed in sequence with water, methyl alcohol and ethyl alcohol, and fixed on a thermometer with a teflon yarn. The atmosphere was purged with nitrogen gas and, then, maintained at 178° C. for 24 hours with stirring at 300 revolutions per minute. After cooling the vessel to room temperature, the testpiece was taken out, washed in sequence with water, methyl alcohol and ethyl alcohol, and dried. For the testpiece, the surface area, weight loss (weights before and after the test) and corrosion rate were measured.

For comparison, the results of corrosion tests (Experiments Nos. 6 and 7) performed in the same manner except that sulfuric acid was used in place of phosphoric acid are also shown in Table 1. In that case, the corrosion rate was rather greater in mixed acid systems and the rate was acid concentration-dependent.

TABLE 1

| Experiment No. | Aqueous acid solution | | Test results | | |
|---|---|---|---|---|---|
| | Phosphoric acid concentration (wt %) | Boric acid concn. (wt %) | Surface area (cm²) | Weight loss (mg) | Corrosion rate (mm/year) |
| 1 | 1.0 | 25.0 | 12.5 | 2.0 | 0.07 |
| 2 | 1.0 | 0 | 11.0 | 5.7 | 0.24 |
| 3 | 4.0 | 20.0 | 11.7 | 2.8 | 0.11 |
| 4 | 4.0 | 0 | 12.6 | 11.6 | 0.42 |
| 5 | 4.0 | 10.0 | 11.6 | 29.4 | 1.17 |
| 6 Sulfuric acid | 0.4 | 20.0 | 17.8 | 228.9 | 16.81 |
| 7 Sulfuric acid | 0.4 | 0 | 17.8 | 186.7 | 14.57 |

Since isobutene has a critical temperature of 144.7° C. and is in the gaseous form under the reaction conditions, it is required, in performing the reaction to dissolve the gaseous isobutene efficiently in the acidic aqueous solution. For this purpose, it is sufficient to cause efficient gas-liquid contact, for example by vigorous stirring of the acidic aqueous solution, with a baffle plate or plates inserted as necessary. For this purpose, it is efficient to further make coexist in the reaction zone a glycol ether of the general formula $$R^2O(CH_2CHO)_nR^3 \quad \text{(I)}$$
$$\overset{|}{R^1}$$

wherein $R^1$ is a hydrogen atom or a methyl group, $R^2$ and $R^3$ each is a hydrogen atom or an alkyl group containing 1 to 4 carbon atoms and n is an integer of 2 to 15 provided that at least one of $R^1$, $R^2$ and $R^3$ is an alkyl group and that the total number of carbon atoms contained in the formula is at least 8. Thus, addition of said glycol ether to the acidic aqueous solution in the reaction zone brings about smooth contact between isobutene with the acidic aqueous solution in the reaction zone, whereby an increased isoprene yield is brought about. Said glycol ether is added generally in an amount of about 5 to 15 percent by weight based on the acidic aqueous solution. The improvement in contact between isobutene and the acidic aqueous solution as caused by the addition of the glycol ether is presumably due to the fact that said glycol ether has excellent compatibility with both isobutene and the acidic aqueous solution.

Referring to general formula (I), examples of the alkyl group containing 1 to 4 carbon atoms as $R^2$ and $R^3$ are methyl, ethyl, n-propyl, isopropyl and n-butyl. It is necessary that at least one of $R^1$, $R^2$ and $R^3$ is an alkyl group. If $R^1$, $R^2$ and $R^3$ are at the same time hydrogen atoms, the compatibility of the glycol ether to isobutene becomes reduced so that the effect of addition thereof cannot be expected any more. In general formula (I), n is required to be an integer of 2 to 15. If n is 1, the effect of addition cannot be expected as in the case in which $R^1$, $R^2$ and $R^3$ are each at the same time a hydrogen atom and moreover the glycol ether is disadvantageously distilled off during the reaction. If n exceeds 15, the compatibility of the glycol ether to the acidic aqueous solution disadvantageously becomes reduced. The total number of carbon atoms contained in general formula (I) is required to be at least 8, so that the kind of each of $R^1$, $R^2$ and $R^3$ and the value of n should be decided so as to meet this requirement. When the total number of carbon atoms is smaller than 8, the glycol ether has a decreased compatibility to isobutene, which results in a decreased effect of addition of the glycol ether, and moreover is disadvantageously distilled off during the reaction.

Preferred examples of the glycol ether are polypropylene glycol having an average molecular weight of 700, tripropylene glycol monomethyl ether, tetraethylene glycol dimethyl ether, diethylene glycol diethyl ether and diethylene glycol monobutyl ether.

When the reaction is conducted for a prolonged period of time, high-boiling byproducts formed in trace amounts during the reaction, especially tar-like substances, are accumulated in the acidic aqueous solution. The high-boiling point byproducts may be separated from the acidic aqueous solution containing high-boiling byproducts accumulated in the reaction zone (it is sometimes referred to as "reaction mixture" in the following description), for example by allowing the reaction mixture to stand in the reaction vessel or by taking out a part of the reaction mixture and transferring the same to a decanter, for instance, followed by separation of the high-boiling byproducts therein. However, since the high-boiling byproducts are close in specific gravity to the acidic aqueous solution, it is difficult to separate them by treating the reaction mixture as it is by the conventional method making use of the difference in specific gravity, such as decantation. Moreover, since said high-boiling byproducts have a property of solidifying at room temperature, their handling after separation is very troublesome. Therefore, the use of a diluent having a low specific gravity is recommendable in the separation of the high-boiling byproducts. Preferable as such diluent is the residue obtained from the organic layer resulting from condensation of the vapor from the reaction zone by distilling off the unreacted starting materials and isoprene therefrom or part thereof (hereinafter each referred to simply as "solvent"), for this solvent is a byproduct from the process according to the invention, therefore is well compatible with the above-mentioned high-boiling byproducts and does not require any particular consideration for the separation and recovery thereof. More particularly, said solvent is obtained as the residue after removal of the unreacted starting materials and isoprene from the distillate organic layer coming from the reaction zone by distillation and contains, among others, 4-methyl-5,6-dihydro-2H-pyran, methyl isopropyl ketone, 2-methylbutanal, 2,6-dimethyl-2,5-heptadiene, 2,6-dimethyl-1,5-heptadiene, 3-methyl-3-buten-1-ol and 2-methyl-3-buten-2-ol. Furthermore, it contains compounds containing 4 to 15 carbon atoms and having such functional groups as hydroxyl, carbonyl, ether linkage and carbon-to-carbon double bond. This distillation residue may be used as it is as the solvent, or part thereof may be separated therefrom and the remaining portion may be used as the solvent.

There is no particular limitation on the amount of the solvent. However, too small an amount will results in a small difference in specific gravity between the solution containing the high-boiling byproducts dissolved therein and the acidic aqueous solution, and in an increased viscosity of said solvent, which is disadvantageous from the processability standpoint. When the solvent is added in an excessive amount, isoprene and other desired components dissolved in the acidic aqueous solution are extracted with the solvent and a recovery procedure of isoprene and other desired components becomes necessary. From these viewpoints, the solvent is added generally in an amount of 20 to 500 g per kilogram of formaldehyde to be fed or, more specifically, in an amount of 0.5 to 3 times the weight of the high-boiling byproducts formed.

The separation of the high-boiling byproducts from the acidic aqueous solution using the solvent can be effected, for instance, by allowing the reaction mixture in the reaction vessel, or by extracting a part of the reaction mixture and transferring to a decanter, extraction tower or the like, where the high-boiling byproducts are separated. The place where the solvent is to be added can be selected depending on the separation method employed.

In practicing the invention on an industrial scale, it is necessary to supply heat by an appropriate means, for instance by circulating the acidic aqueous solution existing in the reaction vessel through a heat exchanger disposed outside the reaction vessel, since heat is required in large amounts for effecting the reaction and distilling off isoprene, water and other low-boiling components. However, when said acidic aqueous solution is heated by circulating the same through an external heat exchanger, the temperature of the acidic aqueous solution in the heat exchanger rises to a level exceeding the optimal reaction condition. As a result, side reactions proceed to an increased extent within the heat exchanger and eventually a decrease in isoprene yield results. It has now been found that this problem can be solved by feeding at least a part of $C_4$ to be subjected to reaction, together with the acidic aqueous solution taken out from the reaction vessel, to the heat exchanger and, after heating, introducing the $C_4$-aqueous solution mixture into the reaction vessel. The minimum amount of $C_4$ to be fed to the heat exchanger depends on the amount of heat to be supplied to the heat exchanger. Besides the temperature rise in the acidic aqueous solution in the heat exchanger, the difference, among others, in comparison with regard to the starting materials and product between the reaction vessel inside and the heat exchanger is also a factor causing side reactions to proceed within the heat exchanger. To solve this problem, the heat exchanger volume should preferably be as small as possible. For that reason, the amount of heat to be given in the heat exchanger should preferably be as small as possible. The heat energy required for the progress of the reaction and the heat energy required for distilling off isoprene, water and other low-boiling components vary depend on whether the starting materials are in the gaseous or liquid form. When all the starting materials are fed to the reaction zone wholly in the gaseous form, the amount of heat to be given is minimal. However, experiments performed by the present inventors revealed that when an aqueous formaldehyde solution employed as the formaldehyde source is vaporized and introduced into a reactor, formaldehyde consumption takes place during the vaporization. In view of the above fact, it is preferable to feed the aqueous fermaldehyde solution to the reaction zone in the liquid form, while C$_4$ and water (exclusive of the water contained in the aqueous formaldehyde solution) are preferably fed to the reaction zone in the gaseous form. By doing so, the heat energy to be given in the heat exchanger can advantageously be reduced.

As is mentioned above, the reaction in the process according to the present invention is carried out by feeding C$_4$, FA and water into the acidic aqueous solution either continuously or intermittently while distilling off isoprene, together with water, unreacted starting materials and other low-boiling components from the reaction zone. Since C$_4$ is used in excess over FA and water is also used in the process, the excess C$_4$ and water are distilled off, together with isoprene, from the reaction zone. Therefore, in the process according to the invention on a commercial scale, a large amount of heat is released from the reaction zone in company with the vapor therefrom. Such a large amount of heat can be recovered effectively and very efficiently in the following manner: First, the vapor from the reaction zone, especially water vapor contained therein, is condensed, whereby the heat energy possessed of by the vapor is recovered. Then, the heat energy possessed of by the uncondensed vapor from the reaction zone is used as the heat source for vaporizing the starting isobutene and/or the heat source for recovering the unreacted isobutene by distillation from the organic layer obtained from the condensate of the vapor from the reaction zone by phase separation.

In recovering the heat energy possessed of by the vapor from the reaction zone, the vapor from the reaction zone is allowed to condense stepwise under almost the same pressure as in the reaction zone, whereby the heat energy possessed of by said vapor from the reaction zone is recovered effectively. Thus, the above-mentioned vapor from the reaction zone is first allowed to condense partly at a temperature adequate for the condensation of water in said vapor from the reaction zone, whereby the latent heat of water is recovered and at the same time the sensible heat of the vapor from the reaction zone is recovered. The heat recovery can be effected by subjecting the vapor from the reaction zone to heat exchange with water to produce steam or by directly using the vapor from the reaction zone as the heat source for reboiler of a distillation column to be used in the recovery of isobutene, the recovery of tertiary butanol or in the recovery or purification of isoprene by introducing said vapor into said reboiler. The amount of steam which can be produced by heat exchange between the vapor from the reaction zone and water is almost equal in weight to the amount of water contained in said vapor, and the steam so generated can be used as the heat source for recovering isobutene, tertiary butanol or isoprene or for purifying isoprene. In the heat exchange between the vapor from the reaction zone and water, steam portions differing in pressure and therefore useful for different purposes can be produced when said vapor from the reaction zone is condensed multistepwise.

Of the water obtained by partial condensation of the vapor from the reaction zone, a necessary amount is generally recycled to the reaction vessel while the remaining portion of water is sent to a step of recovering unreacted reactants, in which step tertiary butanol and formaldehyde are recovered.

The heat energy of the uncondensed portion of the vapor from the reaction zone is used as the heat source for vaporizing the starting isobutene and/or for recovering the unreacted isobutene by distillation from the organic layer obtained from the condensate of the vapor from the reaction zone by phase separation. The vaporization of the starting isobutene can be effected by subjecting isobutene to heat exchange with the uncondensed portion of the vapor from the reaction zone. Feeding the vaporized starting isobutene to the reaction vessel causes reduction in the heat load on the heat exchanger attached to the reaction vessel and furthermore facilitates the dispersion of isobutene into the acidic aqueous solution. A method generally used for supplying a necessary amount of heat to a reactor comprises circulating a reaction mixture through a heat exchanger disposed externally to the reactor. When vaporized isobutene is fed to the reactor through said heat exchanger, as mentioned above, the heat exchanger temperature required for the evaporation of the acidic aqueous solution can be lowered. The heat of condensation obtainable from the uncondensed portion of the vapor from the reaction zone before or after use thereof for the vaporization of isobutene can be used as the heat source for recovering isobutene from the unreacted isobutene-containing organic layer by distillation. Said unreacted isobutene-containing organic layer can be obtained by phase separation of the condensate of that portion of the vapor from the reaction zone which remains after partial condensation of said vapor, which condensate results from the use of said vapor portion as the heat source for vaporizing isobutene or for recovering unreacted isobutene by distillation. Besides said organic layer, an aqueous layer is obtained at the same time. This aqueous layer is sent to a step of recovering unreacted reactants, where tertiary butanol and formaldehyde are recovered. Since most of the heat required for distilling off water from the reaction zone can be recovered by partially condensing the vapor from the reaction zone, the amount of heat required to produce a unit amount of isoprene is decided by the ratio C/F between the reactants to be fed to the reaction zone. Thus, the amount of C$_4$ fed to the reaction zone determines the amount of heat required for the vaporization of isobutene and the recovery of isobutene and tertiary butanol.

Figure 1:
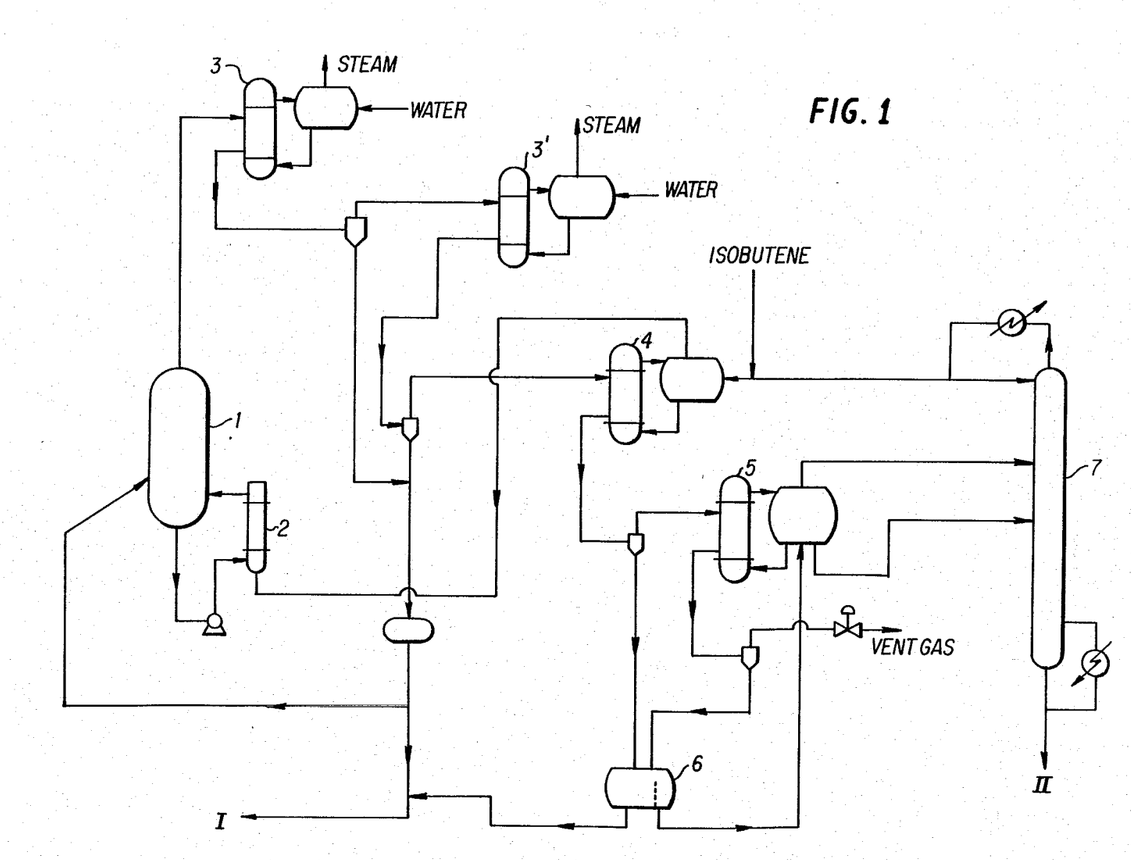

By way of example, a system for the heat recovery from the vapor from the reaction zone is illustrated in FIG. 1.

The vapor from a reactor (1) is introduced into heat exchangers (3) and (3'), where steam is generated. Of the water condensed in (3) and (3'), a required amount is recycled to the reactor and the remaining portion is sent to a step of recovering tertiary butanol and FA. The uncondensed portion of the vapor from the reaction zone, which comes from (3) and (3'), is introduced into a heat exchanger (4), where part of said uncondensed portion is condensed, whereby isobutene, a starting material, is vaporized. The vaporized isobutene is fed to a heat exchanger (2) disposed externally to the reactor. That portion of the vapor from the reaction zone which remains still uncondensed and comes from (4) is introduced into a heat exchanger (5). The condensate formed in (4) is led to a decanter (6), where the condensate separates into an organic layer and an aqueous layer. The organic layer is preheated in (5) and then fed to a distillation column (7), where unreacted isobutene is recovered. The aqueous layer is sent to a step (I) of recovering tertiary butanol and FA. The condensate formed in (5) is led to (6) and is separated into an organic layer and an aqueous layer as in the case of the condensate formed in (4). The bottom liquid from (7) is sent to a step (II) of recovering and purifying isoprene and recovering tertiary butanol.

The process according to the present invention produces highly pure isoprene, which is very useful as the starting material for the manufacture of polyisoprene and terpenes and terpenoid compounds, among other.

Having generally described this invention, a further understanding can be obtained by reference to certain specific examples which are provided herein for purpose of illustration only and are not intended to be limitative of this invention unless otherwise specified.

EXAMPLE 1

The reaction apparatus used was a 750-ml pressure reactor made of glass and equipped with raw material inlet tubes, water inlet tube, thermometer, baffle plate (bubbler), magnetic stirrer and vapor outlet tube. With the vapor outlet tube, there were connected two distillate receptacles (one for preliminary run and the other for quantitative determination) via a condenser. The reactor was charged with 350 g of 3.2% (by weight) aqueous phosphoric acid, and the contents were heated at 178° C. under a pressure of 16.3 kg/cm$^2$. The vapor pressure of 3.2% (by weight) aqueous phosphoric acid at 178° C. is 9.6 kg/cm$^2$. To the reactor, there were fed isobutene at the rate of 201 ml/hr, 27.67% (by weight) aqueous formaldehyde at the rate of 27 ml/hr, and water at the rate of 31.8 ml/hr, while the reactor contents were stirred at the rate of 1,000 revolutions per minute at the above temperature and pressure. The vapor coming out of the reactor was condensed in the condenser and collected in the distillate receptacle for preliminary run. After the reaction was conducted under the above conditions for 3 hours, the distillate passage was changed to the distillate receptacle for quantitative determination and sampling was performed for 2 hours. To constantly maintain the pressure, the vapor was withdrawn through a purge valve and, in sampling, the purged gas was introduced into a trap cooled with dry ice and acetone, where the gas was caused to be absorbed by n-butyl ether. During the above sampling hours, the pressure, temperature and liquid level were kept almost constant. The distillate in the receptacle for quantitative determination was allowed to separate into an aqueous phase and an organic phase, and both the phases were analyzed. The aqueous layer was analyzed for formaldehyde content by the sodium sulfite method and for tertiary butanol content by gas chromatography (internal standard method). The organic layer was analyzed for isobutene, tertiary butanol, isoprene and byproducts contents by gas chromatography (internal standard method). The liquid collected in the trap was also analyzed for isobutene and isoprene contents by gas chromatography (internal standard method). The results were as follows:

| | |
|---|---|
| Isobutene fed | 241.5 g (4,312 millimoles) |
| Formaldehyde fed | 16.24 g (541 millimoles) |
| Water fed (inclusive of water in aqueous formaldehyde) | 106.0 g (5,889 millimoles) |
| Isobutene distilled off (inclusive of isobutene in trap) | 191.7 g (3,423 millimoles) |
| Tertiary butanol distilled off | 27,98 g (378 millimoles) |
| Formaldehyde distilled off | 0.292 g (9.7 mmoles) |
| Isoprene distilled off (inclusive of isoprene in trap) | 25.82 g (380 millimoles) |
| Water distilled off | 107.1 g (5,950 millimoles) |
| C$_4$ fed/formaldehyde fed (moles/mole) | 8.0 |
| Water distilled off/C$_4$ fed (moles/mole) | 1.38 |
| Formaldehyde feed rate per kg of acidic aqueous solution (moles/hr) | 0.77 |
| Formaldehyde conversion (%) | 98.2 |

| Product selectivity (%) | Formaldehyde basis | C$_4$ basis |
|---|---|---|
| Isoprene | 71.5 | 74.4 |
| 4-Methyl-5,6-dihydro-2H—pyran | 7.0 | 3.7 |
| Methyl isopropyl ketone | 2.1 | 2.2 |
| 2-Methylbutanal | 0.5 | 0.5 |
| 2,6-Dimethyl-2,5-heptadiene | 0.8 | 1.7 |
| 2-Methyl-3-buten-2-ol | 0.5 | 0.5 |
| 3-Methyl-3-buten-1-ol | 0.5 | 0.5 |

EXAMPLE 2 TO EXAMPLE 24

Using the same apparatus as used in Example 1, the procedure of Example 1 was followed except that the reaction conditions were varied. The results obtained are shown in Table 2 and Table 3. In cases where the reaction pressure exceeded 20 kg/cm$^2$, a stainless steel (SUS316) vessel was used in place of the glass reactor vessel.

TABLE 2

| Example | 2 | 3 | 4 | 5 | 6 | 7 | 8 | 9 | 10 | 11 | 12 | 13 |
|---|---|---|---|---|---|---|---|---|---|---|---|---|
| Acid | Phosphoric acid | Phosphoric acid | Phosphoric acid | Phosphoric acid | Phosphoric acid | Phosphoric acid | Phosphoric acid | Phosphoric acid | Phosphoric acid | Phosphoric acid | Sulfuric acid | Tungstosilicic acid |
| Acid concentration (wt %) | 3.2 | 3.1 | 3.1 | 3.2 | 7.5 | 25 | 0.35 | 1.5 | 5.0 | 6.0 | 1.0 | 2.5 |
| Temperature (°C.) | 178 | 178 | 178 | 178 | 168 | 153 | 205 | 178 | 178 | 178 | 168 | 168 |
| Vapor pressure of acidic aqueous solution [Pw] (kg/cm$^2$) | 9.6 | 9.6 | 9.6 | 9.6 | 7.5 | 5.0 | 17.5 | 9.7 | 9.6 | 9.6 | 7.6 | 7.6 |
| Reaction pressure [P] (kg/cm$^2$) | 17.1 | 16.9 | 16.1 | 14.7 | 12.2 | 8.0 | 29 | 15.9 | 16.1 | 15.8 | 12.6 | 12.6 |
| P/Pw | 1.78 | 1.76 | 1.68 | 1.53 | 1.63 | 1.60 | 1.66 | 1.64 | 1.68 | 1.65 | 1.66 | 1.66 |
| Isobutene/t-butanol (moles/moles) | 100/0 | 100/0 | 100/0 | 100/0 | 100/0 | 100/0 | 100/0 | 100/0 | 100/0 | 100/0 | 100/0 | 100/0 |
| C$_4$ fed/formaldehyde fed (moles/mole) | 10.6 | 13.1 | 7.3 | 8.1 | 10.0 | 10.1 | 10.0 | 8.0 | 9.0 | 9.0 | 10.0 | 10.0 |
| Formaldehyde feeding rate (moles/kg · hr) | 0.76 | 0.77 | 0.76 | 0.76 | 0.76 | 0.51 | 0.76 | 0.32 | 1.49 | 1.50 | 0.76 | 0.76 |
| Distillate water/C$_4$ fed | 1.22 | 1.26 | 1.41 | 1.78 | 1.50 | 1.58 | 1.40 | 1.50 | 1.44 | 1.44 | 1.50 | 1.50 |

TABLE 2-continued

| Example | 2 | 3 | 4 | 5 | 6 | 7 | 8 | 9 | 10 | 11 | 12 | 13 |
|---|---|---|---|---|---|---|---|---|---|---|---|---|
| (moles/mole) | | | | | | | | | | | | |
| Formaldehyde conversion (%) | 98.1 | 97.8 | 97.9 | 96.8 | 97.0 | 97.2 | 96.0 | 98.1 | 97.4 | 97.8 | 97.2 | 97.0 |
| Isoprene selectivity (%) (formaldehyde basis) | 73.4 | 75.0 | 70.4 | 70.5 | 73.0 | 70.3 | 73.0 | 72.3 | 70.8 | 71.1 | 73.5 | 71.1 |
| Isoprene selectivity (%) ($C_4$ basis) | 75.9 | 77.3 | 74.4 | 76.2 | 75.2 | 73.7 | 72.3 | 73.5 | 74.8 | 73.4 | 74.8 | 72.7 |

TABLE 3

| Example | 14 | 15 | 16 | 17 | 18 | 19 | 20 | 21 | 22 | 23 | 24 |
|---|---|---|---|---|---|---|---|---|---|---|---|
| Acid | p-toluene-sulfonic acid | Boric acid | Boric acid | Potassium hydrogen sulfate | Boric acid | Boric acid | Boric acid | Sulfuric | Phosphoric | Boric acid | Boric acid |
| Acid concentration (wt %) | 3.0 | 36 | 35 | 7.5 | 40 | 30 | 40 | 1.0 | 3.0 | 37.5 | 44.4 |
| Temperature (°C.) | 168 | 180 | 180 | 168 | 170 | 198 | 168 | 178 | 178 | 180 | 170 |
| Vapor pressure of acidic aqueous solution [Pw] (kg/cm$^2$) | 7.6 | 8.7 | 8.7 | 7.5 | 6.6 | 13.8 | 6.3 | 9.7 | 9.6 | 8.4 | 6.3 |
| Reaction pressure [P] (kg/cm$^2$) | 12.6 | 14.0 | 13.3 | 12.5 | 11.2 | 16.6 | 14.0 | 19.4 | 23.0 | 14.8 | 10.8 |
| P/Pw | 1.66 | 1.61 | 1.53 | 1.67 | 1.70 | 1.20 | 2.22 | 2.0 | 2.40 | 1.76 | 1.71 |
| Isobutene/t-butanol (moles/moles) | 100/0 | 100/0 | 100/0 | 100/0 | 100/0 | 100/0 | 100/0 | 100/0 | 100/0 | 100/0 | 100/0 |
| $C_4$ fed/formaldehyde fed (moles/mole) | 10.0 | 10.2 | 10.0 | 10.0 | 15.1 | 10.0 | 10.2 | 10.0 | 10.0 | 10.0 | 10.0 |
| Formaldehyde feeding rate (moles/kg · hr) | 0.76 | 0.47 | 0.36 | 0.76 | 0.36 | 0.77 | 0.71 | 2.86 | 1.90 | 0.77 | 0.77 |
| Distillate water/$C_4$ fed (moles/mole) | 1.50 | 1.33 | 1.55 | 1.50 | 1.40 | 4.50 | 0.82 | 0.95 | 0.71 | 1.30 | 1.40 |
| Formaldehyde conversion (%) | 98.0 | 97.0 | 98.0 | 97.2 | 97.1 | 81.3 | 99.4 | 97.9 | 98.6 | 97.5 | 95.7 |
| Isoprene selectivity (%) (formaldehyde basis) | 71.5 | 70.1 | 70.3 | 72.1 | 73.4 | 69.5 | 65.7 | 70.6 | 68.8 | 68.0 | 66.0 |
| Isoprene selectivity (%) ($C_4$ basis) | 73.0 | 72.5 | 71.9 | 74.3 | 74.0 | 76.3 | 65.4 | 73.9 | 69.7 | 69.2 | 68.0 |

EXAMPLE 25 TO EXAMPLE 28

Using the same apparatus as used in Example 1, the procedure of Example 1 was repeated except that the isobutene was wholly or partly replaced by tertiary butanol and that the reaction conditions were varied. The results obtained are shown in Table 4.

TABLE 4

| | Example | | | |
|---|---|---|---|---|
| Acid | 25 Sulfuric acid | 26 Phosphoric acid | 27 Boric acid | 28 Sulfuric acid |
| Acid concentration (wt %) | 1.0 | 3.2 | 40 | 0.5 |
| Temperature (°C.) | 168 | 178 | 170 | 175 |
| Vapor pressure of acidic aqueous solution [Pw] (kg/cm$^2$) | 7.6 | 9.6 | 6.6 | 9.0 |
| Reaction pressure [P] (kg/cm$^2$) | 12.0 | 15.6 | 9.7 | 10.3 |
| P/Pw | 1.58 | 1.63 | 1.47 | 1.14 |
| Isobutene/t-butanol (moles/moles) | 0/100 | 75/25 | 0/100 | 0/100 |
| C/F (moles/mole) | 8.0 | 8.0 | 10.0 | 3.3 |
| Formaldehyde feeding rate (moles/kg · hr) | 0.75 | 0.75 | 0.77 | 0.22 |
| Distillate water/$C_4$ fed (moles/mole) | 1.70 | 1.50 | 2.12 | 7.05 |
| Formaldehyde conversion (%) | 97.9 | 98.1 | 94.1 | 96.1 |
| Isoprene selectivity (%) (formaldehyde basis) | 73.8 | 71.6 | 72.8 | 65.1 |
| Isoprene selectivity (%) ($C_4$ basis) | 75.0 | 72.9 | 75.2 | 69.5 |

COMPARATIVE EXAMPLES 1-3

Comparative isoprene synthesis runs were conducted by the same procedure as used in Example 1. The results obtained are shown in Table 5.

TABLE 5

| | Comparative Example | | |
|---|---|---|---|
| Acid | 1 Phosphoric acid | 2 Phosphoric acid | 3 Sulfuric acid |
| Acid concentration (wt %) | 7.5 | 3.0 | 0.5 |
| Temperature (°C.) | 168 | 178 | 175 |
| Vapor pressure of acidic aqueous solution [Pw] (kg/cm$^2$) | 7.5 | 9.6 | 9.0 |
| Reaction pressure [P] (kg/cm$^2$) | 23.0 | 28.8 | 15.4 |
| P/Pw | 3.07 | 3.0 | 1.71 |
| Isobutene/t-butanol (moles/moles) | 100/0 | 100/0 | 100/0 |
| $C_4$ fed/formaldehyde fed (moles/mole) | 8.0 | 10.0 | 2.5 |
| Formaldehyde feeding rate (moles/kg · hr) | 0.32 | 0.76 | 0.76 |
| Distillate water/$C_4$ fed (moles/mole) | 0.50 | 0.48 | 1.41 |
| Formaldehyde conversion (%) | 99.9 | 99.7 | 99.1 |
| Isoprene selectivity (%) (formaldehyde basis) | 33.1 | 52.4 | 43.9 |
| Isoprene selectivity (%) ($C_4$ basis) | 23.1 | 41.5 | 44.9 |

EXAMPLE 29

The reaction apparatus used was a 750-ml pressure glass vessel equipped with raw material inlet tube, water inlet tube, thermometer, stainless steel (SUS316)

test piece (5 cm × 1 cm × 0.3 cm) (also serving as a baffle plate), magnetic stirrer and gas outlet tube. Distillate receptacles (one for preliminary run and the other for quantitative determination) were connected with the gas outlet tube via a condenser. The reactor was charged with 60 g of boric acid, 3.0 g of phosphoric acid and 237 g of water, and the contents were heated at 180° C. under a pressure of 15.6 kg/cm$^2$. There was thus prepared an aqueous mixed acid solution containing 20 weight percent of boric acid and 1.0 weight percent of phosphoric acid. The above pressure was maintained through delicate pressure control by introducing nitrogen gas before feeding raw materials and by purging the nitrogen gas during the reaction. The vapor pressure of the above mixed acid solution at 178° C. is 9.3 kg/cm$^2$.

While feeding isobutene at the rate of 129 g/hr and 12.2% (by weight) aqueous formaldehyde at the rate of 56.5 g/hr to the reactor, the reactor contents were stirred at the rate of 1,000 revolutions per minute at the above temperature and pressure. The aqueous vapor distilled off from the reactor was condensed in the condenser and collected in the receptacle for preliminary run. After the reaction was conducted in the above manner for 3 hours, the distillate passage was changed to the receptacle for quantitative determination, followed by sampling for 2 hours. The reaction pressure was adjusted by gas withdrawal. During the sampling, the purged gas was introduced into a trap cooled with dry ice and acetone and allowed to be absorbed by n-butyl ether there. During the above period, the pressure, temperature and liquid level within the reactor were constant. The distillate in the receptacle for quantitative determination was allowed to separate into an aqueous phase and an organic phase. The aqueous phase was analyzed for formaldehyde by the sodium sulfite method and for tertiary butanol by gas chromatography (internal standard method). The organic phase was analyzed for isobutene, tertiary butanol, isoprene and byproducts by gas chromatography (internal standard method). The liquid collected in the trap was also analyzed for isobutene and isoprene by gas chromatography (internal standard method). The testpiece was washed in sequence with water, methyl alcohol and ethyl alcohol, then dried, and weighed for calculation of the weight loss. The results obtained are shown in Table 6.

EXAMPLES 30–32

The reaction was carried out in the same manner as in Example 29 using the same reactor as used in Example 29 except that the phosphoric acid and boric acid concentrations were varied. The results obtained are shown in Table 6.

TABLE 6

|  | Example | | | |
|---|---|---|---|---|
|  | 29 | 30 | 31 | 32 |
| Phosphoric acid concentration (wt %) | 1.0 | 1.0 | 1.0 | 0.75 |
| Boric acid concentration (wt %) | 20.0 | 25.0 | 15.0 | 25.0 |
| Reaction temperature (°C.) | 178 | 178 | 178 | 178 |
| Reaction pressure [P] (kg/cm$^2$) | 15.6 | 15.0 | 15.6 | 14.7 |
| Vapor pressure of acidic aq. soln. at reaction temperature [Pw] (kg/cm$^2$) | 9.3 | 9.2 | 9.4 | 9.2 |
| P/Pw | 1.68 | 1.63 | 1.66 | 1.60 |
| Isobutene fed/formaldehyde fed (moles/mole) | 10 | 10 | 10 | 10 |
| Formaldehyde feeding rate (moles/kg acidic aq. soln. hr) | 0.77 | 0.77 | 0.77 | 0.77 |
| Formaldehyde conversion (%) | 97.4 | 98.2 | 97.0 | 97.3 |
| Isoprene selectivity (%) | | | | |
| Formaldehyde basis | 71.1 | 70.8 | 70.0 | 69.0 |
| C$_4$ basis | 72.6 | 72.3 | 72.3 | 70.3 |
| Testpiece corrosion rate (mm/year) | 0.09 | 0.07 | 0.10 | 0.06 |

EXAMPLE 33

The same apparatus as used in Example 29 was used. The reactor was charged with 120 g of boric acid, 150 g of water and 15 g of polypropylene glycol (product of Nippon Oil & Fat Co.; average molecular weight 700, vapor pressure at 20° C. less than 0.01 mmHg), and the contents were heated at 170° C. under a pressure of 9.7 kg/cm$^2$. The above pressure was maintained by fine adjustment by introducing nitrogen gas before raw materials feeding and by purging the nitrogen gas during the reaction. The vapor pressure of the above aqueous boric acid solution at 170° C. is 6.2 kg/cm$^2$.

While feeding isobutene at the rate of 122 g/hr and 11.36% (by weight) aqueous formaldehyde at the rate of 57.7 g/hr to the reactor, the reactor contents were stirred at the rate of 1,000 revolutions per minute at the above temperature and pressure. The aqueous vapor coming distilled off from the reactor was condensed in the condenser and collected in the receptacle for preliminary run. After the reaction was conducted for 3 hours, the distillate passage was changed to the receptacle for quantitative determination, followed by sampling for 2 hours. The reaction pressure was controlled by gas withdrawal and, during the sampling period, the vapor withdrawn was introduced into a trap cooled with dry ice and acetone and caused to be absorbed by n-butyl ether there. During the above period, the pressure, temperature and liquid level within the reactor were constant. The distillate collected in the receptacle was allowed to separate in an aqueous phase and an organic phase. The aqueous phase was analyzed for formaldehyde by the sodium sulfite method and for tertiary butanol by gas chromatography (internal standard method). The organic phase was analyzed for isobutene, tertiary butanol, isoprene and byproducts by gas chromatography (internal standard method). The liquid collected in the trap was also analyzed for isobutene and isoprene by gas chromatography (internal standard method). The stainless steel test piece for corrosion testing was washed with water, acetone, methyl alcohol and ethyl ether in that order, dried and weighed for calculation of the weight loss. The results obtained are shown in Table 7.

EXAMPLE 34

The reaction was carried out in the same manner as in Example 33 except that 30 g of diethylene glycol monobutyl ether (vapor pressure at 20° C.: 0.01 mmHg) in place of polypropylene glycol in Example 33 and that the isobutene and 11.36% (by weight) aqueous formaldehyde feeding rates were 129 g/hr and 60.7 g/hr, respectively. The results obtained are also shown in Table 7.

TABLE 7

| | Example | |
|---|---|---|
| | 33 | 34 |
| Reaction conditions | | |
| Amount of boric acid charged (g) | 120 | 120 |
| Amount of water charged (g) | 150 | 150 |
| Additive | Polypropylene glycol | Diethylene glycol monobutyl ether |
| Amount of additive (g) | 15 | 30 |
| Additive/aqueous boric acid solution (wt %) | 5.5 | 11.1 |
| Reaction temperature (°C.) | 170 | 170 |
| Reaction pressure [P] (kg/cm$^2$) | 10.7 | 10.5 |
| Vapor pressure of aqueous boric acid solution at reaction temperature [Pw] (kg/cm$^2$) | 6.3 | 6.3 |
| P/Pw | 1.70 | 1.67 |
| C$_4$ fed/formaldehyde fed (moles/mole) | 10 | 10 |
| Formaldehyde feeding rate (moles/kg liquid mixture · hr) | 0.767 | 0.767 |
| Results | | |
| Formaldehyde conversion (%) | 94.9 | 94.0 |
| Isoprene selectivity (%) | | |
| Formaldehyde basis | 71.5 | 70.8 |
| C$_4$ basis | 73.0 | 71.9 |
| Testpiece corrosion rate (mm/year) | 0.06 | 0.05 |

EXAMPLE 35

The reaction apparatus used was composed of two 750-ml pressure glass reaction vessels connected to each other by means of a thermally insulated pipe (for vapor). Each reaction vessel (reactor) was equipped with isobutene inlet tube (for the second reactor, inlet tube for the vapor from the first reactor), aqueous formaldehyde solution inlet tube, baffle plate, thermometer and magnetic stirrer.

Each of the above two reactors was charged with 187.5 g of water and 112.5 g of boric acid. The contents in the first reactor were heated at 180° C. at a pressure of 15.5 kg/cm$^2$ and the contents in the second reactor at the same temperature at a pressure of 14.7 kg/cm$^2$. Thus was prepared 37.5% (by weight) aqueous boric acid. The above-mentioned pressures were maintained by introducing nitrogen gas, with a valve inserted between the two reactors. The vapor pressure of 37.5% (by weight) boric acid at 180° C. was 8.4 kg/cm$^2$ and its pH was 1.2. To the first reactor, there were fed isobutene and 6.93% (by weight) aqueous formaldehyde at the rates of 257.6 g/hr (4.60 moles/hr) and 99.6 g/hr (0.23 mole/hr), respectively. After the entering of the aqueous vapor from the first reactor into the second reactor was confirmed, 29.4% (by weight) aqueous formaldehyde was fed to the second reactor at the rate of 23.5 g/hr (0.23 mole/hr). The reaction was carried out in this manner for 2.5 hours while stirring at 1,000 revolutions per minute at the above-specified pressure and temperature. The aqueous vapor from the second reactor was condensed in a condenser and collected in a receptacle. The pressure was kept constant by fine control by means of purging the nitrogen gas within the system. The liquid level of the acidic aqueous solution was almost constant during the reaction. During the above period, the vapor from the first reactor was sampled and analyzed. The distillate collected in the receptacle during the period beginning from 1.5 hours from the start of the reaction and the time of completion of the reaction as well as the substance accompanied by the purged nitrogen gas (substance introduced into a dry ice-acetone trap and absorbed by n-butyl ether therein) was analyzed for evaluation of the reaction results. Thus, the distillate was allowed to separate into an aqueous phase and an organic phase. The aqueous phase was subjected to gas chromatography (internal standard method) and also analyzed for unreacted formaldehyde by the sodium sulfite method. The organic layer and the the substance in the above-mentioned trap were analyzed by gas chromatography (internal standard method). The results obtained are shown in Table 8.

EXAMPLES 36 AND 37

The reaction was carried out in the same manner and under the same conditions as in Example 35 using the same apparatus as used in Example 35 except that the ratio of isobutene fed to formaldehyde fed and according the water feeding rate were varied. The results obtained are shown in Table 8.

TABLE 8

| | Example 35 | | Example 36 | | Example 37 | |
|---|---|---|---|---|---|---|
| | First reactor | Second reactor | First reactor | Second reactor | First reactor | Second reactor |
| Reaction pressure [P] (kg/cm$^2$) | 15.5 | 14.7 | 15.8 | 13.5 | 15.5 | 13.2 |
| P/Pw | 1.84 | 1.75 | 1.88 | 1.61 | 1.85 | 1.57 |
| Feeding rate | | | | | | |
| Isobutene (moles/hr) | 4.60 | — | 3.68 | — | 2.76 | — |
| Formaldehyde (moles/hr) | 0.23 | 0.23 | 0.23 | 0.23 | 0.23 | 0.23 |
| Water (moles/hr) | 5.14 | 0.92 | 3.70 | 0.91 | 3.17 | 0.93 |
| C/F in each reactor (moles/mole) | 20.0 | 18.7 | 16.0 | 14.6 | 12.0 | 10.7 |
| Isobutene fed/formaldehyde fed (moles/mole) | 10.0 | | 8.0 | | 6.0 | |
| Formaldehyde conversion (%) | 97.8 | | 96.3 | | 96.5 | |
| Isoprene selectivity (%) (formaldehyde basis) | 71.8 | | 68.0 | | 65.4 | |
| Isoprene selectivity (%) | 72.8 | | 69.0 | | 67.5 | |

TABLE 8-continued

|  | Example 35 | | Example 36 | | Example 37 | |
| --- | --- | --- | --- | --- | --- | --- |
|  | First reactor | Second reactor | First reactor | Second reactor | First reactor | Second reactor |
| (C$_4$ basis) | | | | | | |

EXAMPLES 38-40

The reaction was carried out in the same manner and under the same conditions as in Example 35 except that 3.0% (by weight) aqueous phosphoric acid was used in place of aqueous boric acid, that the reaction temperature was 178° C. and that the reaction pressure and raw material and water feeding rates were varied as indicated in Table 9. The vapor pressure of 3.0% (by weight) aqueous phosphoric acid at 178° C. was 9.6 kg/cm$^2$ and its pH was 1.3. The results obtained are shown in Table 9.

TABLE 9

|  | Example 38 | | Example 39 | | Example 40 | |
| --- | --- | --- | --- | --- | --- | --- |
|  | First reactor | Second reactor | First reactor | Second reactor | First reactor | Second reactor |
| Reaction pressure [P] (kg/cm$^2$) | 16.3 | 15.7 | 16.8 | 16.0 | 17.0 | 16.5 |
| P/Pw | 1.70 | 1.63 | 1.75 | 1.67 | 1.77 | 1.72 |
| Feeding rate | | | | | | |
| Isobutene (moles/hr) | 2.76 | — | 3.68 | — | 4.60 | — |
| Formaldehyde (moles/hr) | 0.23 | 0.23 | 0.23 | 0.23 | 0.23 | 0.23 |
| Water (moles/hr) | 3.68 | 0.46 | 4.60 | 0.46 | 5.52 | 0.46 |
| C/F in each reactor (moles/mole) | 12.0 | 10.8 | 16.0 | 14.6 | 20.0 | 18.5 |
| Isobutene fed/ formaldehyde fed (moles/mole) | 6.0 | | 8.0 | | 10.0 | |
| Formaldehyde conversion (%) | 98.4 | | 98.2 | | 98.0 | |
| Isoprene selectivity (%) (formaldehyde basis) | 70.8 | | 73.6 | | 75.6 | |
| Isoprene selectivity (%) (C$_4$ basis) | 72.4 | | 74.9 | | 76.9 | |

EXAMPLE 41

The reaction apparatus used was composed of three 750-ml pressure glass vessels (reactors) connected in series with piping for the passage of vapor under thermal insulation. Each reactor was equipped with isobutene inlet tube (for the second and the third reactor, inlet tube for vapor from the first and the second reactor, respectively), aqueous formaldehyde inlet tube, baffle plate, thermometer and magnetic stirrer.

Each of the above three reactors was charged with 300 g of 3.0% (by weight) aqueous phosphoric acid, and the contents were heated at 178° C. and at a pressure of 16.5 kg/cm$^2$ (for the first reactor), 16.0 kg/cm$^2$ (for the second reactor) or 15.5 kg/cm$^2$ (for the third reactor). The above pressure levels were maintained by introducing nitrogen gas and inserting valves between the first and the second reactor and between the second and the third reactor. The vapor pressure of 3.0% (by weight) aqueous phosphoric acid at 178° C. is 9.6 kg/cm$^2$.

To the first reactor isobutene and 6.65% (by weight) aqueous formaldehyde were fed at the rates of 231.8 g/hr (4.14 moles/hr) and 103.7 g/hr (0.23 mole/hr), respectively. After the entering of the aqueous vapor from the first reactor into the second reactor was confirmed, 48.1% (by weight) aqueous formaldehyde was fed to the second reactor at the rate of 14.35 g/hr (0.23 mole/hr). Similarly, after confirming the entrance of the aqueous vapor from the second reactor into the third reactor, 48.1% (by weight) aqueous formaldehyde was fed to the third reactor at the rate of 14.35 g/hr (0.23 mole/hr). The reaction was carried out in this manner for 2.5 hours while stirring the contents of each reactor at 1,000 revolutions per minute at the above-mentioned pressure and temperature. The aqueous vapor from the third reactor was condensed in the condenser and collected in the receptacle. The pressure in each reactor was kept constant by fine adjustment by purging the nitrogen gas. The surface of the acidic aqueous solution in each reactor remained at an almost constant level during the reaction. The reaction results obtained in the same manner as in Example 35 are shown in Table 10.

EXAMPLE 42

The reaction was carried out in the same manner and under the same conditions as in Example 41 using the same apparatus as used in Example 41 except that the ratio of isobutene fed to formaldehyde fed and accordingly the amount of water fed were varied. The results obtained are shown in Table 10.

TABLE 10

|  | Example 41 | | | Example 42 | | |
| --- | --- | --- | --- | --- | --- | --- |
|  | First reactor | Second reactor | Third reactor | First reactor | Second reactor | Third reactor |
| Reaction pressure [P] (kg/cm$^2$) | 16.5 | 16.0 | 15.5 | 15.9 | 15.2 | 14.6 |
| P/Pw | 1.71 | 1.67 | 1.61 | 1.65 | 1.58 | 1.52 |

TABLE 10-continued

|  | Example 41 | | | Example 42 | | |
| --- | --- | --- | --- | --- | --- | --- |
|  | First reactor | Second reactor | Third reactor | First reactor | Second reactor | Third reactor |
| Feeding rate |  |  |  |  |  |  |
| Isobutene (moles/hr) | 4.14 | — | — | 2.76 | — | — |
| Formaldehyde (moles/hr) | 0.23 | 0.23 | 0.23 | 0.23 | 0.23 | 0.23 |
| Water (moles/hr) | 5.29 | 0.46 | 0.46 | 3.91 | 0.46 | 0.46 |
| C/F in each reactor (moles/mole) | 18.0 | 16.6 | 15.5 | 12.0 | 10.8 | 9.7 |
| Isobutene fed/formaldehyde fed (moles/mole) |  | 6.0 |  |  | 4.0 |  |
| Formaldehyde conversion (%) |  | 98.1 |  |  | 98.1 |  |
| Isoprene selectivity (%) (formaldehyde basis) |  | 71.6 |  |  | 67.5 |  |
| Isoprene selectivity (%) ($C_4$ basis) |  | 73.8 |  |  | 70.7 |  |

EXAMPLE 43

The reaction was carried out in the same manner and under the same conditions as in Example 38 using the same apparatus as used in Example 35 except that formaldehyde was fed to the first and the second reactor in a proportion of 2:1 and that the formaldehyde feeding rate and the amount of water fed were varied. The results obtained are shown in Table 11.

EXAMPLE 44

The reaction was carried out in the same manner and under the same conditions as in Example 43 except that a 1,000-ml pressure glass reactor was used as the first reactor and was charged with 400 g of 3.0% (by weight) aqueous phosphoric acid, that the second reactor was charged with 200 g of aqueous phosphoric acid having the same concentration, and that the ratio in acidic aqueous solution volume between the first and the second reactor was kept at 2:1. The results obtained are shown in Table 11.

EXAMPLE 45

The reaction was carried out in the same manner and under the same conditions as in Example 38 using the same apparatus as used in Example 35 except that formaldehyde was fed to the first and the second reactor in a proportion of 1:2 and that the formaldehyde feeding rate and the amount of water fed were varied. The results obtained are shown in Table 11.

EXAMPLE 46

The reaction was carried out in the same manner and under the same conditions as in Example 45 except that a 1,000-ml pressure glass reaction vessel was used as the second reactor and was charged with 400 g of 3.0% (by weight) aqueous phosphoric acid, that the first reactor was charged with 200 g of aqueous phosphoric acid having the same concentration and that the liquid volume ratio between the first and the second reactor was 1:2. The results obtained are shown in Table 11.

TABLE 11

|  | Example 43 | | Example 44 | | Example 45 | | Example 46 | |
| --- | --- | --- | --- | --- | --- | --- | --- | --- |
|  | First reactor | Second reactor | First reactor | Second reactor | First reactor | Second reactor | First reactor | Second reactor |
| Amount of aqueous acid solution charged (g) | 300 | 300 | 400 | 200 | 300 | 300 | 200 | 400 |
| Reaction pressure [P] (kg/cm$^2$) | 16.0 | 15.6 | 16.0 | 15.6 | 16.5 | 15.6 | 16.5 | 15.6 |
| P/Pw | 1.67 | 1.63 | 1.67 | 1.63 | 1.85 | 1.63 | 1.85 | 1.63 |
| Feeding rate |  |  |  |  |  |  |  |  |
| Isobutene (moles/hr) | 2.76 | — | 2.76 | — | 2.76 | — | 2.76 | — |
| Formaldehyde (moles/hr) | 0.31 | 0.15 | 0.31 | 0.15 | 0.15 | 0.31 | 0.15 | 0.31 |
| Water (moles/hr) | 3.88 | 0.30 | 3.88 | 0.30 | 3.45 | 0.62 | 3.45 | 0.62 |
| C/F in each reactor (moles/mole) | 8.9 | 15.6 | 8.9 | 15.7 | 18.4 | 8.3 | 18.4 | 8.3 |
| Isobutene fed/formaldehyde fed (moles/mole) | 6.0 |  | 6.0 |  | 6.0 |  | 6.0 |  |
| Formaldehyde feeding rate in first reactor (moles/kg · hr) | 1.03 |  | 0.87 |  | 0.50 |  | 0.75 |  |
| Formaldehyde feeding rate in second reactor (moles/kg · hr) | 0.50 |  | 0.75 |  | 1.03 |  | 0.78 |  |
| Formaldehyde conversion (%) | 98.9 |  | 98.4 |  | 97.9 |  | 98.4 |  |
| Isoprene selectivity (%) (formaldehyde basis) | 69.2 |  | 70.3 |  | 70.5 |  | 70.6 |  |
| Isoprene selectivity (%) ($C_4$ basis) | 70.9 |  | 71.8 |  | 73.0 |  | 72.3 |  |

EXAMPLE 47

The reaction apparatus used was composed of four 750-ml pressure glass reaction vessels (reactors) connected in series by means of piping for the passage of vapor under thermal insulation. Each reactor was equipped with isobutene inlet tube (for the second, third and fourth reactor, inlet tube for the vapor from the preceding reactor), aqueous formaldehyde inlet tube, baffle plate, thermometer and magnetic stirrer.

Each of the above four reactors was charged with 300 g of 3.0% (by weight) aqueous phosphoric acid and heated at 178° C. and at a pressure of 16.5 kg/cm$^2$ (first reactor), 16.0 kg/cm$^2$ (second reactor), 15.5 kg/cm$^2$ (third reactor) or 15.0 kg/cm$^2$ (fourth reactor). The above pressure was maintained by introducing nitrogen gas and inserting a valve between every two neighboring reactors. The vapor pressure of 3.0% (by weight) aqueous phosphoric acid at 178° C. is 9.6 kg/cm$^2$.

To the first reactor, there were fed isobutene and 5.15% (by weight) aqueous formaldehyde at the rates of 309.1 g/hr (5.52 moles/hr) and 134.0 g/hr (0.23 mole/hr), respectively. After confirming the entering of the aqueous vapor from the first reactor into the second reactor, 48.1% (by weight) aqueous formaldehyde was fed to the second reactor at the rate of 14.35 g/hr (0.23 mole/hr). Similarly, after confirming the entering of the aqueous vapor from the second reactor into the third reactor, 48.1% (by weight) aqueous formaldehyde was fed to the third reactor at the rate of 14.35 g/hr (0.23 mole/hr). Furthermore, after confirming the entering of the aqueous vapor from the third reactor into the fourth reactor, 48.1% (by weight) aqueous formaldehyde was fed to the fourth reactor at the rate of 14.35 g/hr (0.23 mole/hr). The reaction was carried out in that manner for 2.5 hours while stirring the contents of each reactor at 1,000 revolutions per minute at the above-specified pressure and temperature. The aqueous vapor from the fourth reactor was condensed in the condenser and collected in the distillate receptacle. The pressure in each reactor was kept constant by fine adjustment thereof by purging the nitrogen gas. The acid aqueous solution surface remained at an almost constant level during the reaction. The reaction results obtained in the same manner as in Example 35 are shown in Table 12.

TABLE 12

|  | First reactor | Second reactor | Third reactor | Forth reactor |
|---|---|---|---|---|
| Reaction pressure [P] (kg/cm$^2$) | 16.5 | 16.0 | 15.5 | 15.0 |
| P/Pw | 1.71 | 1.67 | 1.61 | 1.56 |
| Feeding rate |  |  |  |  |
| Isobutene (moles/hr) | 5.52 | — | — | — |
| Formaldehyde (moles/hr) | 0.23 | 0.23 | 0.23 | 0.23 |
| Water (moles/hr) | 7.06 | 0.46 | 0.46 | 0.46 |
| C/F in each reactor (moles/mole) | 24.0 | 22.5 | 21.2 | 19.7 |
| Isobutene fed/ formaldehyde fed (moles/mole) |  |  | 6.0 |  |
| Formaldehyde conversion (%) |  |  | 98.1 |  |
| Isoprene selectivity (%) (formaldehyde basis) |  |  | 72.0 |  |
| Isoprene selectivity (%) (C$_4$ basis) |  |  | 73.5 |  |

EXAMPLE 48

The reaction apparatus used was a 120-liter reactor made of Hastelloy G-3 equipped with raw material inlet means, distillate vapor outlet line, distillate condenser, stirrer, thermometer, pressure gauge, multi-tubular heat exchager and distillate receptacle. The total capacity of the acidic aqueous solution circulation line and the multi-tubular heat exchanger was 115 liter. The reactor, circulation line and multi-tubular heat exchanger were charged with 160 kg of water and while a 10% aqueous solution of boric acid was continuously fed into the reaction vessel, aqueous boric acid solution was introduced to the heat exchanger via the circulation line at a rate of 2.0 m$^3$/hr. Thus, under stirring, the water was evaporated by using steam as the heating medium. With the increasing concentration of aqueous boric acid solution in the reaction system, the pressure was increased to elevate the aqueous boric acid solution temperature. When the concentration of boric acid had reached 40%, the supply of aqueous boric acid was suspended and the internal pressure of the system was elevated with nitrogen gas to 10.5 kg/cm$^2$ and the internal temperature increased to 170° C. After the start of evaporation, the liquid level in the reaction vessel was kept constant throughout.

Then, isobutene was admitted into an isobutene evaporator at a rate of 62 kg/hr and the resulting vapor was introduced into the multi-tubular heat exchanger. At the same time, 25.38% aqueous formaldehyde solution and water were fed to the reaction apparatus at the rates of 10.05 kg/hr and 26.3 kg/hr, respectively, so as to initiate the reaction. The reaction was conducted for 6 hours. Then, the distillate outlet was switched to the quantitative receptacle and the reaction was further continued for 2.5 hours. During this period, the pressure was maintained at 10.5 kg/cm$^2$ by means of a pressure regulator. Incidentally, the vapor pressure of a 40% aqueous solution of boric acid at 170° C. is 6.6 kg/cm$^2$.

As to the distillate in the quantitative receptacle, the aqueous phase was taken out and its weight was measured. The weight of the organic phase was determined by withdrawing a portion thereof into a pressure-resistant bottle, measuring its specific gravity, and multiplying the result with the volume of the phase.

The amount of formaldehyde in the aqueous phase was analyzed by the sodium sulfite method, and that of tertiary butanol by gas chromatography (internal standard method). The amounts of isoprene, isobutene, tertiary butanol and byproducts in the organic phase were also analyzed by gas chromatography (internal standard method). The results of the above reaction were as follows.

| Isobutene fed | 2760 moles |
|---|---|
| Formaldehyde fed | 212.6 moles |
| C$_4$ fed/formaldehyde fed (moles/mole) | 13.0 |
| Water fed (inclusive of water in aqueous formaldehyde) | 3655 moles |
| Formaldehyde distilled off | 5.6 moles |
| Isoprene distilled off | 140.1 moles |
| Water distilled off | 3418 moles |
| Water in vapor/C$_4$ fed (moles/mole) | 1.24 |
| Feeding rate of formaldehyde per kg of acidic aqueous solution | 0.49 mole/hr |
| % Conversion of formaldehyde | 97.4% |
| % Yield of isoprene | 67.7% |

(based on consumed formaldehyde)

EXAMPLE 49

The same reaction equipment as used in Example 48 was employed. The reaction apparatus, circulation line and multi-tubular heat exchanger were filled with 150 kg of a 3.0% aqueous solution of phosphoric acid, and under stirring, the solution was circulated at a flow rate of 2.0 m$^3$/hr with heating to 178° C. at a pressure of 16.0 kg/cm$^2$. Then, isobutene was fed into an isobutene evaporator at a rate of 51 kg/hr and the resultant vapor was introduced into the multi-tubular heat exchanger. At the same time, 25.38% aqueous formaldehyde and water were fed to the reaction apparatus at the rates of 13.48 kg/hr and 13.2 kg/hr, respectively, so as to initiate the reaction. After 10 hours of reaction, the distillate outlet was switched to the quantitative receptacle and sampling was conducted for 2 hours. The liquid level within the reaction apparatus was maintained at the level that prevailed immediately after the start of isobutene feed and the pressure was maintained at 16.0 kg/cm$^2$ by means of a pressure regulator. Incidentally, the vapor pressure of a 3.0% aqueous solution of phosphoric acid at 178° C. is 9.6 kg/cm$^2$. Analysis was then performed in the same manner as Example 48. The results are presented below.

| | | |
|---|---|---|
| Iasobutene fed | 1817 | moles |
| Formaldehyde fed | 228.0 | moles |
| C$_4$ fed/formaldehyde fed (moles/mole) | 8.0 | |
| Water fed (inclusive of water in aqueous formaldehyde) | 2574 | moles |
| Formaldehyde distilled off | 4.8 | moles |
| Isoprene distilled off | 153.8 | moles |
| Water distilled off | 2540 | moles |
| Water in vapor/C$_4$ fed (moles/mole) | 1.40 | |
| Feeding rate of formaldehyde per kg of acidic aqueous solution | 0.76 | mole/hr |
| % Conversion of formaldehyde | 97.9% | |
| % Yield of isoprene (based on consumed formaldehyde) | 68.9% | |

EXAMPLE 50

The reaction equipment used was a 120-liter reactor made of Hastelloy G-3 equipped with raw material inlet means, distillate outlet means, distillate condenser, stirrer, thermometer, pressure gauge, acidic aqueous solution outlet, acidic aqueous solution circulation line, heat exchanger and distillate receptacle. The total capacity of the acidic aqueous solution circulation line and the heat exchanger was 25 liter. A 3% aqueous solution of phosphoric acid (89 kg) was introduced into the reactor, circulation line and heat exchanger, and heated by the heat exchanger with stirring until the internal temperature of the reactor registered 178° C. at the pressure of 16.0 kg/cm$^2$. Then, isobutene was fed into an isobutene evaporator at a rate of 31 kg/hr and the resultant vapor was fed to the reactor via a water evaporator. The water evaporator was supplied with water at 8.6 kg/hr and the water vaporized was fed to the reactor along with the isobutene vapor. Then, a 27.67% aqueous solution of formaldehyde was introduced into the reactor at a rate of 7.3 kg/hr to initiate the reaction. The vapor output from the reactor was condensed in the condenser and fed to the distillate receptacle. After 6 hours of reaction, the condensate outlet was switched to the quantitative distillate receptacle and the reaction was further conducted for 3 hours. During this operation, the pressure and the internal temperature of the reactor were maintained at 16.0 kg/cm$^2$ and 178° C., respectively. Incidentally, the vapor pressure of a 3.0% aqueous solution of phosphoric acid at 178° C. is 9.6 kg/cm$^2$.

From the distillate in the quantitative distillate receptacle, the aqueous phase was taken and its weight determined. The weight of the organic phase was determined by sampling a portion thereof into a pressure-resistant bottle, measuring its specific gravity and multiplying the result with the volume of the phase.

The amount of formaldehyde in the aqueous phase was analyzed by the sodium sulfite method, and that of tertiary butanol by gas chromatography (internal standard method). The amounts of isoprene, isobutene, tertiary butanol and byproducts in the organic phase were analyzed by gas chromatography (internal standard method). The results of the reaction were as follows.

| | | |
|---|---|---|
| Isobutene fed | 1646 | moles |
| Formaldehyde fed | 200.4 | moles |
| C$_4$ fed/formaldehyde fed (moles/mole) | 8.2 | |
| Water fed (inclusive of water in aqueous formaldehyde) | 2331 | moles |
| Formaldehyde distilled off | 4.0 | moles |
| Isoprene distilled off | 140.9 | moles |
| Water distilled off | 2420 | moles |
| Water in vapor/C$_4$ fed (moles/mole) | 1.47 | |
| Feeding rate of formaldehyde per kg of acidic aqueous solution | 0.75 | mole/hr |
| % Conversion of formaldehyde | 98.0% | |
| % Yield of isoprene (based on consumed formaldehyde) | 71.7% | |

EXAMPLE 51

(i) Recovery of distillation byproducts

The reaction apparatus used was a 120-liter reactor of Hastelloy G-3 equipped with raw material inlet means, distillate out piping, distillate condenser, stirrer, thermometer, pressure gauge, acidic aqueous solution outlet, acidic aqueous solution circulation line, high-boiling fraction decanter, heat exchanger and decanter-type distillate receptacle. The combined capacity of the acidic aqueous solution circulation line and heat exchanger was 25 liters and the capacity of the high-boiling fraction decanter was 20 liters. The reactor, circulation line, heat exchanger and high-boiling fraction decanter were charged with a total of 120 kg of 3% aqueous phosphoric acid. The charge was heated by means of the heat exchanger with stirring and circulation at a pressure of 16.0 kg/cm$^2$ until the reactor inside temperature reached 178° C. Then, isobutene was fed to an isobutene vaporizer at the rate of 31 kg/hr and the thus-vaporized isobutene was supplied to the reactor through a water evaporator. Water was fed to said water evaporator at the rate of 8.0 kg/hr and vaporized therein and, together with isobutene, fed to the reactor. The reaction was started by feeding 27.67% aqueous formaldehyde to the reactor at the rate of 7.5 kg/hr. The vapor coming out of the reactor was condensed in the condenser and sent to the decanter-type distillate receptacle and allowed therein to separate into an organic phase and an aqueous phase. The organic phase separated was sent to a distillation column, where isobutene was distilled off by continuous distillation. The bottom liquid was cooled and transferred to a drum can. While keeping the temperature and pressure within the reactor constant, the reaction and distillation for isobutene recovery were carried out for 100 hours. During this period, the acidic aqueous solution was circulated at the rate of 15 liters/hr through the overflow-type high-boiling fraction decanter maintained at 160° C. Overflow of a high-boiling fraction was not observed. The bottom liquid collected by the isobutene recovery distillation during the above period amounted to 680 kg. This liquid was further distilled. After isoprene and tertiary butanol were distilled off, there was obtained 105 kg of a residue. Gas chromatography revealed that this residue contained the following components:

| | |
|---|---|
| 4-Methyl-5,6-dihydro-4H—pyran | 24.0% |
| Methyl isopropyl ketone | 11.4% |
| 2,6-Dimethyl-2,5-heptadiene | 5.7% |
| 2,6-Dimethyl-1,5-heptadiene | 3.1% |
| 2-Methyl-3-buten-2-ol | 3.0% |
| 3-Methyl-3-buten-1-ol | 2.1% |

On the other hand, the tar-like high-boiling liquid in the high-boiling fraction decanter was withdrawn after completion of the reaction. The fraction weighed 8.3 kg and, upon cooling to room temperature, lost its flowability and solidified.

(ii) The procedure of (i) above was repeated under the same conditions except that the distillation residue obtained in (i) above was supplied to the circulation line to the high-boiling fraction decanter at the rate of 300 g/hr. After 20 hours of reaction, overflow of an oily substance from the high-boiling fraction decanter was observed. After 100 hours of reaction, said oily substance accumulated weighed 27 kg. This substance did not solidify even when cooled to room temperature.

EXAMPLE 52

A 50-kg portion of the distillation residue obtained in Example 51-(i) was taken and a fraction boiling at up to 122° C. was distilled off to give 33.5 kg of a residue, whereby methyl isopropyl ketone, 2-methyl-3-buten-2-ol and most of 4-methyl-5,6-dihydro-4H-pyran were removed. While feeding the residue to the circulation line to the high-boiling fraction decanter at the rate of 150 g/hr, the reaction was carried out under otherwise the same conditions as in Example 51-(i). After 18 hours of reaction, an oily substance began to overflow from the high-boiling fraction decanter and, after 100 hours of reaction, the oily substance amounted to 18 kg. This substance did not solidify even when cooled to room temperature.

EXAMPLE 53

A test run was performed according to the flowchart shown in FIG. 1.

The apparatus used consisted of a 400-liter stainless steel reactor (1) equipped with raw material inlet means, water inlet piping, thermometer, pressure gauge, stirrer and vapor outlet piping and an external heat exchanger (2) connected with a circulation pump and an isobutene vapor inlet piping. The vapor outlet piping was connected with a series of heat exchangers. The reactor was charged with 188 kg of 3% (by weight) aqueous phosphoric acid, and the reaction was carried out at 180° C. and 16.8 kg/cm$^2$. The vapor pressure of 3% (by weight) aqueous phosphoric acid at 180° C. is 10.1 kg/cm$^2$. The stirrer was driven at 500 revolutions per minute. To the reactor, there were fed continuously 48% (by weight) aqueous formaldehyde at the rate of 8.9 kg/hr, tertiary butanol at the rate of 22.0 kg/hr and circulating water at the rate of 22.7 kg/hr, whereas recovered isobutene vapor was supplied to the external heat exchanger at the rate of 46.6 kg/hr. The rate of flow of the vapor from the reactor was 100 kg/hr. Under these conditions, the heat consumption in the external heat exchanger (2) was $24 \times 10^3$ kcal/hr and the consumption of medium pressure steam (15 kg/cm$^2$) was 51 kg/hr. The vapor from the reactor was condensed stepwise while maintaining its pressure at a level almost equal to that of the reaction system. Thus, the vapor was first introduced into two heat exchanger compartments (3) and (3'), where the vapor was condensed at 170° C. and 140° C., respectively. The amounts of heat exchanged were $6.5 \times 10^3$ kcal/hr and $8.5 \times 10^3$ kcal/hr, respectively and the amounts of steam generated were 13 kg/hr of steam at 4 kg/cm$^2$ and 16 kg/hr of steam at 2.5 kg/cm$^2$, respectively. The condensate from the reactor as produced in the heat exchanger compartment (3) amounted to 31 kg/hr, corresponding almost the whole amount of water evaporated. Thereafter, the uncondensed portion of the vapor from the reactor was introduced in a heat exchanger (4), where the vapor was further partly condensed at 110° C. while isobutene was vaporized. The vaporization of isobutene was conducted at a pressure of 18 kg/cm$^2$ which was somewhat higher than the pressure within the reactor. The heat released by the vapor from the reactor upon condensation in the heat exchanger (4) amounted to $4 \times 10^3$ kcal/hr. The uncondensed vapor portion leaving the heat exchanger (4) amounted to 55 kg/hr and was introduced into a heat exchanger (5) for final condensation at 97° C. The amount of heat released by condensation in this step was $5 \times 10^3$ kcal/hr. Using this heat, the organic layer resulting from phase separation of the combined condensate obtained in the heat exchangers (4) and (5) was preheated prior to feeding the same to a distillation column (7) for recovering unreacted isobutene. The pressure on the liquid supply side of the heat exchanger (5) was maintained at 5.7 kg/cm$^2$, whereby the temperature reached 74° C. In the heat exchanger (5), the isobutene fraction contained in the feed liquid was mostly flushed, and this was supplied in the vapor form to the distillation column (7). In this manner, the heat of condensation of the vapor from the reactor could be utilized very efficiently and the heat consumed in the reaction zone could be almost 100% recovered. The bottom liquid from the distillation column (7) was further distilled for cutting off higher-boiling and lower-boiling fractions to finally give pure isoprene at the rate of 6.7 kg/hr.

REFERENCE EXAMPLE 1

The reaction procedure described in Example 32 of U.S. Pat. No. 3,890,404 was repeated. However, in view of the statement in the Japanese Kokai Tokkyo Koho No. 48-502 by the same applicant and by the overlapped inventorship on the same subjects that a reactor of titanium is an apparatus of choice, a titanium-lined autoclave was used as the reactor.

Thus, the titanium-lined autoclave equipped with a stirrer was charged with 10 g of a 37% aqueous solution of formaldehyde and 68 g of tertiary butanol, and a sealed glass tube containing 2.4 g of ferrous chloride and 26 g of water was put in the autoclave. The autoclave was heated and when its internal temperature reached 160° C., the stirrer was actuated to break the glass tube and initiate the reaction. The reaction was conducted at 160° C. for 18 minutes, after which the reaction mixture was transferred under pressure into a previously ice-cooled dilute aqueous alkali solution, whereby it was rapidly cooled to terminate the reaction. (This procedure was used for cooling the reaction mixture, for it is claimed to cause little losses of the product.) The oil and aqueous layers were separated and independently analyzed by gas chromatography to determine the yield of isoprene. The absolute yield of isoprene was 3.52 g and its % yield based on formaldehyde charge was 42%. Assay for unreacted formaldehyde in the aqueous layer was attempted by the sodium sulfite method but it was found to be below the detection limit.

REFERENCE EXAMPLE 2

The reaction according to Example 2 of Japanese Patent Publication No. 52-30,483 was repeated except that a titanium-lined autoclave was used as the reactor.

The titanium-lined autoclave equipped with a stirrer was charged with 11.5 g of a 26% aqueous solution of formaldehyde, 11.1 g of water and 59.2 g of tertiary butanol, and a sealed glass tube containing 1.13 g of potassium alum and 3 g of water was put in the autoclave. After the top cover was replaced on the autoclave, 33.6 g of isobutene was introduced. The autoclave was heated and when its internal temperature had reached 160° C., the stirrer was actuated to break the glass tube and initiate the reaction. The reaction was conducted at 160° C. for 1 hour, after which the reaction mixture was transferred under pressure into a previously ice-cooled dilute aqueous alkali solution to terminate the reaction.

The yield of isoprene as found by the same procedure as Reference Example 1 was 2.34 g. This value corresponds to 34.5% on the basis of formaldehyde charge. No unreacted formaldehyde was detected.

REFERENCE EXAMPLE 3

The reaction according to Example 1 of Japanese Kokai Tokkyo Koho No. 48-502 was repeated.

A titanium-lined autoclave equipped with a stirrer was charged with 9.2 g of a 26% aqueous solution of formaldehyde, 8.5 g of water and 47.4 g. of tertiary butanol, and a sealed glass tube containing 0.86 g of aluminum chloride hexahydrate and 2.0 g of water was put in the autoclave. After the top cover was replaced on the autoclave, 27 g of isobutene was introduced. Thereafter, the procedure of Reference Example 1 was repeated to conduct the reaction at 160° C. for 30 minutes, after-treat the reaction mixture, and analyze it. The yield of isoprene was 2.55 g and its % yield based on formaldehyde charge was 47%. Unreacted formaldehyde was not detected.

REFERENCE EXAMPLE 4

The reaction according to Example 8 of Japanese Kokai Tokkyo Koho No. 57-130,928 was repeated.

A 1-liter autoclave of stainless steel (SUS-316) equipped with a stirrer was charged with 100 g of tertiary butanol, 38.0 g of a 12.12% aqueous solution of formaldehyde (4.6 g of formaldehyde), 0.09 g of tungstosilicic acid and 142.3 g of water. The autoclave was heated with stirring to 210° C., at which temperature the stirring was stopped immediately and the contents were rapidly cooled. The time required for heating from room temperature to 210° C. was 1 hour. After cooling to room temperature, the reaction mixture was taken into a pressure-resistant glass bottle of 500 ml capacity and the organic layer was separated from the aqueous layer. The organic phase and the aqueous phase which was neutralized beforehand were analyzed by gas chromatography to determine the yields of isoprense. In addition, unreacted formaldehyde in the neutralized aqueous phase was assayed by the sodium sulfite method. The % conversion of formadehyde was 98.2% and the selectivity for isoprene based on formadehyde was 50.2%, and the % yield of isoprene based on formaldehyde charge was 49.3%.

REFERENCE EXAMPLE 5

The reaction according to Example 1 of U.S. Pat. No. 4,067,923 was repeated.

A 300 ml autoclave of stainless steel (SUS-316) equipped with a stirrer was charged with 16.6 g of a 36% aqueous solution of formaldehyde, 50.4 g of a 88% aqueous solution of tertiary butanol and 0.1 g of sulfanilic acid. Then, 33.6 g of isobutene was introduced and the reaction mixture was heated to 130° over a period of 45 minutes and the reaction was conducted at the increased temperature for 20 minutes. The reaction was further conducted at 180° for 40 minutes. The time required for the temperature increase from 130° to 180° C. was 32 minutes. After completion of the reaction, the reaction mixture was rapidly cooled and purged into a dry ice-acetone trap until atmospheric pressure was established. The contents of the autoclave were separated and the oil layer, the water layer and the trap contents were analyzed by gas chromatography. In addition, the aqueous layer was analyzed for formaldehyde by the sodium sulfite method. The % conversion of formaldehyde was 85%, and the selectivity for isoprene based on formaldehyde was 0.8%. The main product was 4,4-dimethyl-1,3-dioxane.

What we claim is:

1. A process for producing isoprene by reacting isobutene and/or tertiary butanol with formaldehyde in an acidic aqueous solution, characterized in:
   (a) that the acidic aqueous solution is present in the reaction zone,
   (b) that isobutene and/or tertiary butanol, a formaldehyde source and water are fed to said reaction zone continuously or intermittently, and
   (c) that isoprene, water, unreacted starting materials and other low-boiling components are distilled off from said reaction zone, the amounts of said isobutene and/or tertiary butanol and formaldehyde source being fed to said reaction zone being such that the isobutene/tertiary butanol-to-formaldehyde molar ratio in the charge is at least 3 and the pressure in the reaction system being maintained at a level 1.1 to 2.5 times the vapor pressure at the reaction temperature of the acidic aqueous solution existing in the reaction zone, said isobutene/tertiary butanol-to-formaldehyde molar ratio being calculated by calculating the amount of the formaldehyde source in formaldehyde equivalent when said source is other than formaldehyde.

2. The process as claimed in claim 1, characterized in:
   (a) that the acidic aqueous solution is present in plural reaction zones connected in series, (b) that isobutene and/or tertiary butanol is fed to the first reaction zone continuously or intermittently while a formaldehyde source and water are fed to each reaction zone continuously or intermittently, (c) that isoprene, water, unreacted starting materials and other low-boiling components are distilled off from each reaction zone except the last one and fed to the subsequent reaction zone, and (d) that isoprene, water, unreacted starting materials and other low-boiling components are distilled off from the last reaction zone, the amounts of said isobutene and/or tertiary butanol and formaldehyde source being fed to each reaction zone being such that the isobutene/tertiary butanol-to-formaldehyde molar ratio in the charge is at least 3 and the pressure in the reaction system being maintained at a level 1.1 to 2.5 times the vapor pressure at the reaction temperature of the acidic aqueous solution existing in the reaction zone, said isobutene/tertiary butanol-to-formaldehyde molar ratio being calculated by calculating the amount of the formaldehyde source in formaldehyde equivalent when said source is other than formaldehyde.

3. The process as claimed in claim 2, wherein the number of the reaction zones is 2, 3 or 4.

4. The process as claimed in claim 1, wherein the feed rate of the formaldehyde source as expressed in terms of the number of moles of formaldehyde per kilogram of the acidic aqueous solution per hour is not more than 3 moles/kg·hr.

5. The process as claimed in claim 1, wherein an aqueous formaldehyde solution is used as the formaldehyde source.

6. The process as claimed in claim 1, wherein the reaction temperature is 150°–220° C.

7. The process as claimed in claim 1, wherein the acidic aqueous solution has a pH of 0.5–2.5.

8. The process as claimed in claim 1, wherein the acidic aqueous solution is an aqueous mixed acid solution containing 15–30 percent by weight of boric acid and 0.5–5 percent by weight of phosphoric acid.

9. The process as claimed in claim 1, wherein a glycol ether of the general formula wherein $R^1$ is a hydrogen atom or a methyl group, $R^2$ and $R^3$ each is a hydrogen atom or an alkyl group containing 1 to 4 carbon atoms and n is an integer of 2 to 15, provided that at least one of $R^1$, $R^2$ and $R^3$ is an alkyl group and the total number of carbon atoms included in the above formula is at least 8, is added, in an amount of 5 to 15 percent by weight, to the acid aqueous solution.

10. The process as claimed in claim 5, wherein a part of the acidic aqueous solution is taken out from the reaction vessel, heated and returned to the reaction vessel, while feeding to the reaction vessel the aqueous formaldehyde solution to be newly fed in the liquid form and isobutene and/or tertiary butanol and water (exclusive of the water contained in the aqueous formaldehyde solution) in the gaseous form, each continuously or intermittently.

11. The process as claimed in claim 1, wherein a part of the acidic aqueous solution in taken out from the reaction vessel, heated together with at least a part of the isobutene and/or tertiary butanol to be fed and then introduced into the reaction vessel in admixture therewith.

12. The process as claimed in claim 1, wherein the residue obtained from the organic layer resulting from condensation of the vapor from the reaction zone by distilling off the unreacted starting materials and isoprene therefrom or a part of said residue is added to the acidic aqueous solution containing high-boiling byproducts accumulated in the reaction zone or a part thereof and the mixture is separated into an acidic aqueous solution and an organic layer containing extracted high-boiling byproducts.

13. The process as claimed in claim 1, wherein the vapor from the reaction zone, especially water vapor contained therein, is condensed, whereby the heat energy possessed of by the vapor is recovered, and the heat energy possessed of by the uncondensed vapor is used as the heat source for vaporizing the starting isobutene and/or heat source for recovering the unreacted isobutene by distillation from the organic layer obtained from the condensate of the vapor from the reaction zone by phase separation.

* * * * *